US011173480B2

(12) United States Patent
Miyamoto et al.

(10) Patent No.: US 11,173,480 B2
(45) Date of Patent: Nov. 16, 2021

(54) CATALYST IN WHICH METAL IS CARRIED ON INORGANIC POROUS BODY HAVING HIERARCHICAL POROUS STRUCTURE, AND METHOD FOR MANUFACTURING SAID CATALYST

(71) Applicant: SnG Inc., Kyoto (JP)

(72) Inventors: Riichi Miyamoto, Kyoto (JP); Hongzhi Bai, Kyoto (JP); Hironao Sajiki, Gifu (JP); Tomohiro Ichikawa, Gifu (JP); Masahiro Mizuno, Gifu (JP); Aya Ogawa, Gifu (JP); Hayato Masuda, Gifu (JP); Tsuyoshi Yamada, Gifu (JP); Tomohiro Matsuo, Gifu (JP); Yutaka Kobayashi, Gifu (JP)

(73) Assignee: SNG INC., Kyoto (JP)

( * ) Notice: Subject to any disclaimer, the term of this patent is extended or adjusted under 35 U.S.C. 154(b) by 0 days.

(21) Appl. No.: 16/651,824

(22) PCT Filed: Sep. 28, 2018

(86) PCT No.: PCT/JP2018/036594
§ 371 (c)(1),
(2) Date: Mar. 27, 2020

(87) PCT Pub. No.: WO2019/066076
PCT Pub. Date: Apr. 4, 2019

(65) Prior Publication Data
US 2020/0246779 A1 Aug. 6, 2020

(30) Foreign Application Priority Data

Sep. 29, 2017 (JP) .............................. JP2017-191417

(51) Int. Cl.
| *B01J 23/44* | (2006.01) |
| *B01J 37/16* | (2006.01) |
| *B01J 21/08* | (2006.01) |
| *B01J 35/02* | (2006.01) |
| *B01J 35/10* | (2006.01) |
| *B01J 37/02* | (2006.01) |
| *C07C 1/22* | (2006.01) |
| *C07C 1/30* | (2006.01) |
| *C07C 5/03* | (2006.01) |
| *C07C 5/08* | (2006.01) |
| *C07C 5/09* | (2006.01) |
| *C07C 29/14* | (2006.01) |
| *C07C 29/143* | (2006.01) |
| *C07C 37/055* | (2006.01) |
| *C07C 41/18* | (2006.01) |
| *C07C 51/09* | (2006.01) |
| *C07C 67/303* | (2006.01) |
| *C07C 209/34* | (2006.01) |

(Continued)

(52) U.S. Cl.
CPC .............. *B01J 37/16* (2013.01); *B01J 21/08* (2013.01); *B01J 23/44* (2013.01); *B01J 35/002* (2013.01); *B01J 35/026* (2013.01); *B01J 35/109* (2013.01); *B01J 37/0203* (2013.01); *B01J 37/0219* (2013.01); *B01J 37/0221* (2013.01); *C07C 1/22* (2013.01); *C07C 1/30* (2013.01); *C07C 5/03* (2013.01); *C07C 5/08* (2013.01); *C07C 5/09* (2013.01); *C07C 29/14* (2013.01); *C07C 29/143* (2013.01); *C07C 37/055* (2013.01); *C07C 41/18* (2013.01); *C07C 51/09* (2013.01); *C07C 67/303* (2013.01); *C07C 209/34* (2013.01); *C07C 209/42* (2013.01); *C07C 227/04* (2013.01); *C07C 231/12* (2013.01); *C07C 269/06* (2013.01); *C07F 7/188* (2013.01); *C07C 2521/08* (2013.01); *C07C 2523/44* (2013.01)

(58) Field of Classification Search
CPC ....... C07C 37/055; C07C 41/18; C07C 51/09; C07C 67/303; C07C 209/34; C07C 209/42; C07C 227/04; C07C 231/12; C07C 269/06; C07C 2521/08; C07C 2523/44; C07F 7/188
See application file for complete search history.

(56) References Cited

U.S. PATENT DOCUMENTS 6,194,650 B1 * 2/2001 Wakayama .............. B01J 21/06
136/256
8,530,369 B2 * 9/2013 Lewis .................. B01J 37/0242
502/150

(Continued)

FOREIGN PATENT DOCUMENTS

| JP | 2000-017442 A | 1/2000 |
| JP | 2010-510060 A | 4/2010 |

(Continued)

OTHER PUBLICATIONS

T. Baumann et al., 354 Journal of Non-Crystalline Solids, 3513-3515 (2008) (Year: 2008).*

(Continued)

Primary Examiner — Alexander R Pagano
(74) Attorney, Agent, or Firm — Paratus Law Group, PLLC

(57) ABSTRACT

A catalyst includes a carrier, and a metal obtained by reducing a metal ion supported on the carrier 1) in a supercritical state or 2) in a polar organic solvent, wherein the carrier is an inorganic porous body having a hierarchical porous structure. By employing the catalyst, it is possible to exhibit better catalytic activity than a conventional catalyst. Heat generation and spontaneous ignition are prevented because no organic porous body is used.

16 Claims, 6 Drawing Sheets

(51) Int. Cl.
*C07C 209/42* (2006.01)
*C07C 227/04* (2006.01)
*C07C 231/12* (2006.01)
*C07C 269/06* (2006.01)
*C07F 7/18* (2006.01)
*B01J 35/00* (2006.01)

(56) References Cited

U.S. PATENT DOCUMENTS

| | | | |
|---|---|---|---|
| 8,809,230 B2 * | 8/2014 | Worsley | B01J 23/755 |
| | | | 502/417 |
| 2007/0281160 A1 * | 12/2007 | Krishna | C04B 35/62665 |
| | | | 428/403 |
| 2010/0140138 A1 | 6/2010 | Chaumonnot et al. | |

FOREIGN PATENT DOCUMENTS

| | | |
|---|---|---|
| JP | 2011-200774 A | 10/2011 |
| JP | 2014-148456 A | 8/2014 |
| JP | 2014148456 A * | 8/2014 |
| JP | 2015-180494 A | 10/2015 |
| JP | 2016-070937 A | 5/2016 |
| JP | 2016070937 A * | 5/2016 |

OTHER PUBLICATIONS

N. Danilina etal.272 Journal of Catalysis, 37-43 (2010) (Year: 2010).*
K. Egeblad, 20 Chem. Mater., 946-960 (2008) (Year: 2008).*
Kumar 4 Materials Today Proceedings, 350-357 (2017) (Year: 2017).*
K. Sing et al., 57 Pure and Applied Chemistry, 603-609 (1985) (Year: 1985).*
K. Matsuyama et al., 130 Journal of Supercritical Fluids, 140-146 (2017) (Year: 2017).*
M. Tenorio et al., 49 Journal of Supercritical Fluids, 369-376 (2009) (Year: 2009).*
Y. Wang et al., 174 Fuel, 17-24 (2016) (Year: 2016).*
A. Feliczak-Guzik, 259 Microporous and Mesoporous Materials, 33-45 (2018) (Year: 2018).*
K. Kusada et al., Journal of the American Chemical Society, 1864-1871 (2014) (Year: 2014).*
Tenorio, M.J. et al., Supercritical $CO_2$ as a reaction and impregnation medium in the synthesis of Pd-$SiO_2$ aerogel inverse opals, The Journal of Supercritical Fluids, 2009, pp. 369-376, vol. 49.
Matsuyama, K. et al., Supercritical fluid-assisted immobilization of Pd nanoparticles in the mesopores of hierarchical porous $SiO_2$ for catalytic applications, The Journal of Supercritical Fluids, 2017, pp. 140-146, vol. 130.
Kusada, K. et al., Solid Solution Alloy Nanoparticles of Immiscible Pd and Ru Elements Neighboring on Rh: Changeover of the Thermodynamic Behavior for Hydrogen Storage and Enhanced CO-Oxidizing Ability, Journal of the American Chemical Society, 2014, pp. 1864-1871, vol. 136.
Monguchi, Y. et al., Recent Development of Palladium-Supported Catalysts for Chemoselective Hydrogenation, Chem, Pharm, Bull., 2017, pp. 2-9, vol. 65, No. 1.
Mori, A. et al., Pd/C-Catalyzed Chemoselective Hydrogenation in the Presence of Diphenylsulfide, Organic Letters, 2006, pp. 3279-3281, vol. 8, No. 15.
Mori, A. et al., Chemoselective hydrogenation method catalyzed by Pd/C using diphenylsulfide as a reasonable catalyst poison, Tetrahedron, 2006, p. 11925-11932, vol. 62.
Ichikawa, T. et al., Development of a Unique Heterogeneous Palladium Catalyst for the Suzuki-Miyaura Reaction using (Hetero)aryl Chlorides and Chemoselective Hydrogenation, Advanced Synthesis & Catalysis, Jun. 2017, pp. 2269-2279, vol. 359.
Aime, S. et al., Dependence of the relaxivity and luminescence of gadolinium and europium amino-acid complexes on hydrogencarbonate and pH, Chem. Commun, 1999, pp. 1047-1048.
Sajiki, S. et al., Highly Chemoselective Hydrogenation with Retention of the Epoxide Function Using a Heterogeneous Pd/C-Ethylenediamine Catalyst and THF, Chem. Eur. J., 2000, pp. 2200-2204, vol. 6, No. 12.

* cited by examiner

——100μm

——30μm

—100μm

—30μm

—10nm

—10nm

CATALYST IN WHICH METAL IS CARRIED ON INORGANIC POROUS BODY HAVING HIERARCHICAL POROUS STRUCTURE, AND METHOD FOR MANUFACTURING SAID CATALYST

CROSS REFERENCE TO PRIOR APPLICATION

This application is a National Stage Patent Application of PCT International Patent Application No. PCT/JP2018/036594 (filed on Sep. 28, 2018) under 35 U.S.C. § 371, which claims priority to Japanese Patent Application No. 2017-191417 (filed on Sep. 29, 2017), which are all hereby incorporated by reference in their entirety.

TECHNICAL FIELD

The present invention relates to a catalyst in which metal is supported on an inorganic porous body having a hierarchical porous structure, and a method for producing the same.

BACKGROUND ART

Conventionally, organic porous bodies and inorganic porous bodies have been used as carriers of various catalysts by taking advantage of their porosity and also widely used as fillers for liquid chromatography columns.

For example, PTL 1 relates to a macroporous monolith, and Claim 1 thereof discloses "a macroporous monolith comprising a skeleton constituted by hydride silica, a macropore presenting a bicontinuous structure with the skeleton; and a hierarchical porous structure of a mesopore and the macropore since the mesopore having an opening on a surface of the skeleton is formed in the skeleton, wherein a hydrogen site based on a Si—H bond is distributed on the surface of the skeleton and inside the mesopore." PTL 1 also discloses the application of the macroporous monolith as a filler for a chromatography separation column (the paragraph [0248] and the like). Claim 6 of PTL 1 discloses "a macroporous monolith comprising: a skeleton constituted by hydride silica or silica gel; a macropore presenting a bicontinuous structure with the skeleton; and a hierarchical porous structure of a mesopore and the macropore since the mesopore having an opening on a surface of the skeleton is formed in the skeleton, wherein a nanoparticle constituted by nickel or metal whose standard electrode potential is positively greater than that of hydrogen is disposed inside the mesopore." Then, Claims 7 to 9 of PTL 1 disclose the applications of the macroporous monolith, in which the specific metal nanoparticle is disposed inside the mesopore, as a catalyst for fuel cells, a catalyst for cross-coupling reaction, and a catalyst for exhaust gas removing devices.

PTL 2 discloses that a granular porous body made of an inorganic porous body having a hierarchical porous structure is used as a filler for a liquid chromatography column, and Claim 1 thereof discloses "an inorganic granular porous body used for a liquid chromatography column to separate peptide, protein or nucleic acid, the granular porous body comprising a skeleton body composed of an inorganic compound with a three-dimensional continuous network structure, and further a bimodal hierarchical porous structure composed of through-holes formed in voids of the skeleton body and pores extending from a surface to the inside of the skeleton body and dispersively formed on the surface, wherein the most frequent pore diameter in pore diameter distribution of the pores is within a range of 2 nm or more and 80 nm or less, the most frequent pore diameter of pore diameter distribution of the through-holes is equal to or greater than five time the most frequent pore diameter of the pores and is within a range of 0.1 μm or more and 10 μm or less, and the particle diameter of the granular porous body is equal to or greater than five time the most frequent pore diameter of the through-holes and is within a range of 20 μm or more and 250 μm or less." Note that PTL 2 does not describe use of the granular porous body as a catalyst carrier.

When the organic porous bodies and the inorganic porous bodies are used as catalyst carriers, a catalyst using an inorganic porous body as a carrier tends to have lower catalytic activity than a catalyst using an organic porous body as a carrier, such as carbon. In this regard, as a technique for enhancing the catalytic activity it is known to support catalytic metal in a supercritical state. Specifically, it is known to dissolve a precursor of a metal nanoparticle in supercritical carbon dioxide having low viscosity and high diffusivity, impregnate the inside of pores of a mesoporous inorganic porous body (an inorganic porous body having no through-holes) with the precursor of the nanoparticle, and then form (support) the metal nanoparticle inside the pores by reduction treatment (PTL3, NPL1).

Although these literatures disclose that the catalytic metal is supported on the mesoporous inorganic porous body in the supercritical state, the enhancement of the catalytic activity by utilizing a supercritical state is limited from these reports. Moreover, these literatures do not discuss any means for enhancing the catalytic activity of a catalyst using, as a carrier, an inorganic porous body having a hierarchical porous structure.

In a case of catalytic reduction such as hydrogenation using a heterogeneous metal catalyst (hereinafter referred to as reduction reaction), there are often a plurality of easily-reduced functional groups, and it is usually difficult to selectively reduce these functional groups. Therefore, in order to selectively reduce only a specific functional group, it is necessary to utilize a catalyst that meets the purpose (NTL 2). For example, there are many known catalysts that can non-selectively reduce reactants such as an epoxide group, a benzyl ether group, a halogen atom (e.g., chlorine, bromine, iodine, or the like) on an aromatic ring or a heteroaromatic ring, a benzyl ester group, a carbonyl group (ketone, aldehyde group) adjacent to an aromatic ring or a heteroaromatic ring, a nitrogen-bonded benzyloxycarbonyl group (N-Cbz group), a nitro group, an alkenyl group, an azido group and an alkyne group. A catalyst that selectively reduces a specific functional group among these, or a catalyst that has no or little effect on a specific functional group has been always demanded in synthetic chemistry. Moreover, a catalyst has been demanded, which reduces only the above specific functional groups non-selectively or selectively, but does not reduce a silyl group when an oxygen-bonded trialkylsilyl group (e.g., an O-trimethylsilyl (O-TMS) group, an O-triethylsilyl (O-TES) group, or the like) is present together with the above functional groups in a molecule. Furthermore, there is no catalyst that does not reduce an epoxide group, a benzyl ether group, a halogen atom (as defined above) on an aromatic ring or a heteroaromatic ring, a benzyl ester group, a carbonyl group (ketone, aldehyde group) adjacent to an aromatic ring or a heteroaromatic ring, or the like, but selectively reduces only a nitro group, an alkenyl group, an azido group, an alkyne group or the like. In addition, there is no catalyst that can selectively reduce only an N-Cbz group if reaction conditions such as temperature and time are selected. Thus, the development of such catalysts has been strongly demanded.

Note that a catalyst using, as a carrier, an organic porous body such as carbon (e.g., a catalyst using carbon as a carrier in which palladium is supported on the carrier (hereinafter, also referred to as a catalyst mainly containing Pd/C)) has high catalytic activity so that the organic carrier itself possibly generates heat, ignites or the like. Thus, it is necessary to take measures such as cooling or wetting with water after use and during storage.

From these points, it is desirable to use a catalyst using an inorganic porous body as a carrier, particular a catalyst using an inorganic porous body having a hierarchical porous structure as a carrier. However, there is still room for improvement in terms of advancement of catalytic activity.

CITATION LIST

Patent Literature

PTL 1: JP2014-148456A
PTL 2: JP2016-070937A
PTL 3: JP2000-017442A

Non-Patent Literature

NPL 1: Kohei Kusada, Hirokazu Kobayashi, Ryuichi Ikeda, Yoshiki Kubota, Masaki Takata, Shoichi Toh, Tomokazu Yamamoto, Syo Matsumura, Naoya Sumi, Katsutoshi Sato, Katsutoshi Nagaoka, and Hiroshi Kitagawa "Solid Solution Alloy Nanoparticles of Immiscible Pd and Ru Elements Neighboring on Rh: Changeover of the Thermodynamic Behavior for Hydrogen Storage and Enhanced CO-Oxidizing Ability", J. Am. Chem. Soc., 2014, 136 (5), pp 1864-1871

NPL 2: Yasunari Monguchi, Tomohiro Ichikawa and Hironao Sajiki "Recent Development of Palladium-Supported Catalysts for Chemoselective Hydrogenation", Chem. Pharm. Bull. 2017, 65. pp 2-9

SUMMARY OF INVENTION

Technical Problem

The present invention has been made in light of such problems, and an object thereof is to provide a catalyst in which metal is supported on an inorganic porous body having a hierarchical porous structure, and a simple method for producing the same.

Solution to Problem

The inventors have intensively studied to achieve the above object. As a result, the inventors have found out that the above object can be achieved when metal particles are supported (immobilized) on an inorganic porous body having a hierarchical porous structure under specific conditions, and have come to accomplish the present invention.

That is, the present invention provides a catalyst according to the following aspects and a method for producing the same.

Item 1
A catalyst comprising:
a carrier, and
a metal obtained by reducing a metal ion supported on the carrier 1) in a supercritical state or 2) in a polar organic solvent,
the carrier being an inorganic porous body having a hierarchical porous structure.

Item 2
The catalyst according to Item 1, wherein the metal is a platinum group element and/or a group 10 element.

Item 3
The catalyst according to Item 1 or 2, wherein a supporting amount of the metal is 0.01 to 30 wt % based on 100 wt % of the catalyst.

Item 4
The catalyst according to any one of Items 1 to 3, wherein a supporting amount of the metal supported 2) in the polar organic solvent is 0.01 to 30 wt % based on 100 wt % of the catalyst Item 5
The catalyst according to any one of Items 1 to 4, wherein the polar organic solvent is at least one selected from the group consisting of methanol, acetonitrile, acetone, 2-propanol and tetrahydrofuran Item 6
The catalyst according to any one of Items 1 to 3, wherein a supporting amount of the metal supported 1) in the supercritical state is 0.01 to 6 wt % based on 100 wt % of the catalyst Item 7
A method for producing a catalyst the method comprising
a step of causing an inorganic porous body having a hierarchical porous structure to support a metal ion 1) in a supercritical state or 2) in a polar organic solvent; and
a step of reducing the metal ion.

Item 8
The method for producing the catalyst according to Item 7, wherein a metal is a platinum group element and/or a group 10 element.

Item 9
The method for producing the catalyst according to Item 7 or 8, wherein a supporting amount of the metal is 0.01 to 30 wt % based on 100 t % of the catalyst.

Item 10
The method for producing the catalyst according to any one of Items 7 to 9, wherein a supporting amount of the metal supported 2) in the polar organic solvent is 0.01 to 30 wt %/o based on 100 wt % of the catalyst Item 11
The method for producing the catalyst according to any one of Items 7 to 10, wherein the polar organic solvent is at least one selected from the group consisting of methanol, acetonitrile, acetone, 2-propenol and tetrahydrofuran Item 12
The method for producing the catalyst according to any one of Items 7 to 9, wherein a supporting amount of the metal supported 1) in the supercritical state is 0.01 to 6 w %/o based on 100 wt % of the catalyst.

Item 13
A method for producing the catalyst according to any one of Items 1 to 6, the method comprising:
a step of causing an inorganic porous body having a hierarchical porous structure to support a metal ion 1) in a supercritical state or 2) in a polar organic solvent; and
a step of reducing the metal ion.

Item 14
A reduction method comprising a step of reducing a reactant by using the catalyst according to any one of Items 1 to 6.

Item 15
A reduction method comprising a step of reducing a reactant (excluding styrene as the reactant) by using the catalyst according to any one of Items 1 to 6.

Item 16
The reduction method according to Item 14 or 15, wherein the reactant is a compound having an alkynyl group, an alkenyl group, an azido group, a nitro group, an N-Cbz group, a ketone group or an aldehyde group adjacent to an aromatic ring or a heteroaromatic ring, a benzyl ester group, a halogen atom on an aromatic ring or a heteroaromatic ring, a benzyl ether group, an epoxide group, or an N-Cbz group, and optionally having in a molecule a substituent of an alkyl group, an aromatic ring or a heteroaromatic ring resistant to reduction.

Item 17
The reaction method according to Item 14 or 15, wherein the reactant is diphenylacetylene, p-ethylnitrobenzene, 1-azido ethylbenzene, p-anisaldehyde, benzophenone, benzyl phenyl ether, benzoyl-D-phenylalanine, 4-chlorodiphenylmethane, styrene oxide, ethylene glycol dibenzyl ether, 2'-nitroacetanilide, 4-azidobenzoic acid, benzyl N-allyl-N-phenylcarbamate, benzyl N-(2-phenethyl)carbamate, phenyl isopropyl ketone, benzyl cinnamate, benzyl benzoate, 4-benzyloxyphenol benzylnoninyl ether, benzyldecanyl ether or cinnamyloxytriethylsilane.

Item 18
A use of the catalyst according to any one of Items 1 to 6 in a reduction reaction for reducing a reactant.

Item 19
The use of the catalyst according to Item 18, wherein the reactant is a compound having an alkynyl group, an alkenyl group, an azido group, a nitro group, an N-Cbz group, a ketone group or an aldehyde group adjacent to an aromatic ring or a heteroaromatic ring, a benzyl ester group, a halogen atom on an aromatic ring or a heteroaromatic ring, a benzyl ether group, an epoxide group, or an N-Cbz group, and optionally having in a molecule a substituent of an alkyl group, an aromatic ring or a heteroaromatic ring resistant to reduction.

Item 20
The use of the catalyst according to Item 18, wherein the reactant is diphenylacetylene, p-ethylnitrobenzene, 1-azido-4-ethylbenzene, p-anisaldehyde, benzophenone, benzyl phenyl ether, benzoyl-D-phenylalanine, 4-chlorodiphenylmethane, styrene oxide, ethylene glycol dibenzyl ether, 2'-nitroacetanilide, 4-azidobenzoic acid, benzyl N-allyl-N-phenylcarbamate, benzyl N-(2-phenethyl)carbamate, phenyl isopropyl ketone, benzyl cinnamate, benzyl benzoate, 4-benzyloxyphenol, benzylnoninyl ether, benzyldecanyl ether or cinnamyloxytriethylsilane.

Advantageous Effects of Invention

The catalysts of the present invention can exhibit better catalytic activities than conventional catalysts by causing an inorganic porous body having a hierarchical porous structure to support metal under specific conditions. Moreover, heat generation and spontaneous ignition are prevented because no organic porous body is used.

DESCRIPTION OF EMBODIMENTS

Figure 1A:
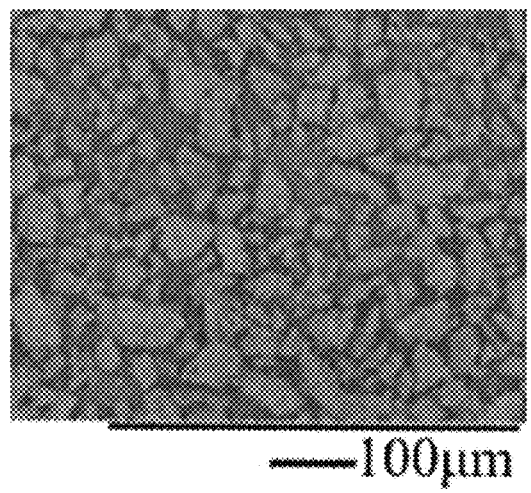
FIG. 1A and FIG. 1B show scanning electron microscope (SEM) photographs of a silica porous body, which has a hierarchical porous structure not supporting metal.
Figure 1B:
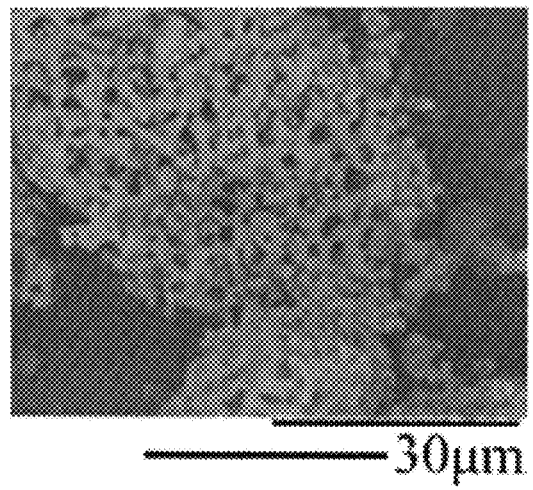
Figure 1C:
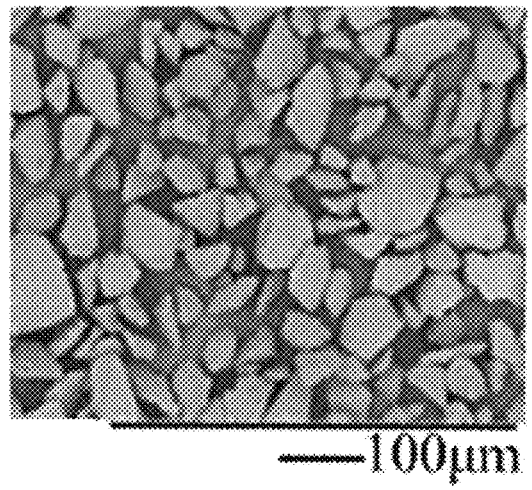
FIG. 1C and FIG. 1D show SEM photographs of a silica porous body, which does not have a hierarchical porous structure not supporting metal. It shows that the silica porous body which has the hierarchical porous structure not supporting metal, has a macroporous structure, whereas the silica porous body, which does not have a hierarchical porous structure not supporting metal, has a smooth surface.
Figure 1D:
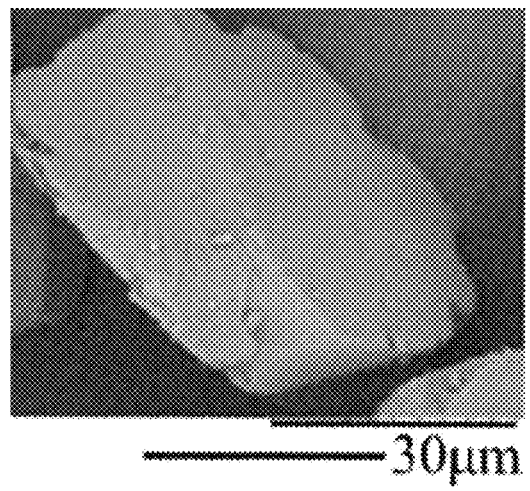
Figure 2A:
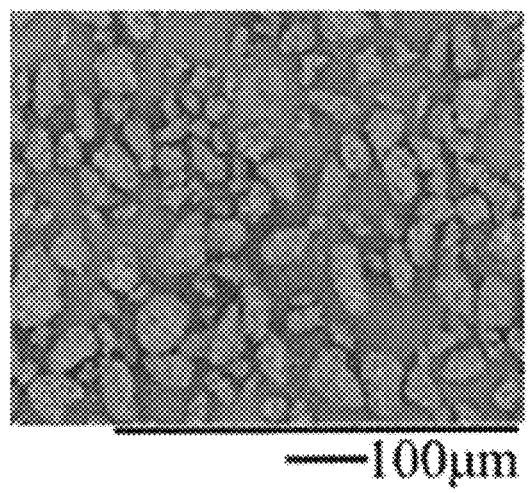
FIG. 2A and FIG. 2B show SEM photographs of a silica gel granular porous body obtained in Example 1, which has a bimodal hierarchical porous structure supporting palladium (Pd).
Figure 2B:
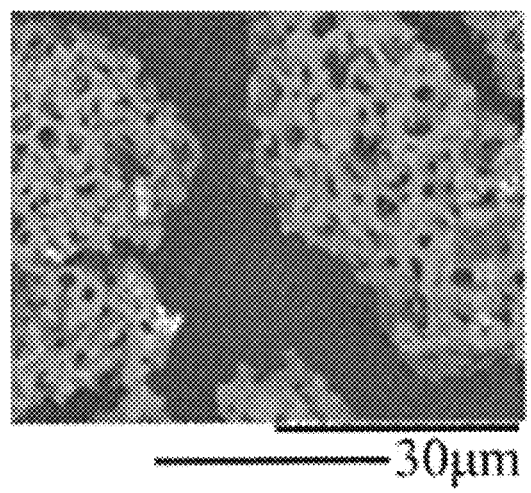
Figure 2C:
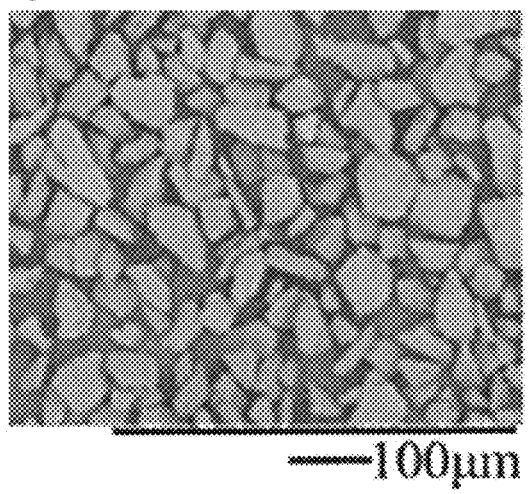
FIG. 2C and FIG. 2D show SEM photographs of a silica gel granular porous body (silica porous body) obtained in Comparative Example 2, which does not have a hierarchical porous structure supporting palladium. It shows that the silica gel granular porous body, which has the bimodal hierarchical porous structure supporting palladium, has a surface shape similar to a surface shape of the silica porous body, which has the hierarchical porous structure not supporting metal in FIG. 1A and FIG. 1B. It also shows that the silica gel granular porous body, which does not have a hierarchical porous structure supporting palladium, has a surface shape similar to a surface shape of a silica porous body, which does not have a hierarchical porous structure not supporting metal in FIG. 1C and FIG. 1D.
Figure 2D:
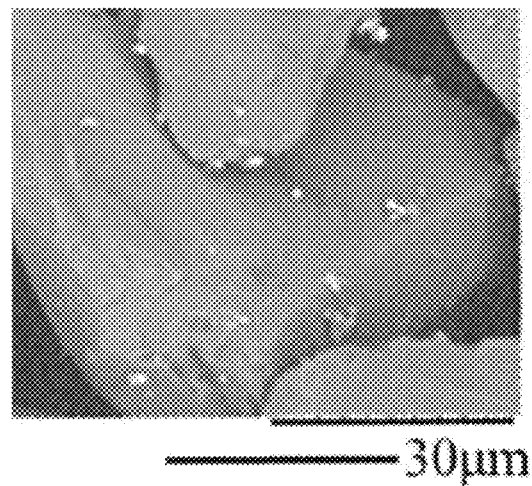
Figure 3A:
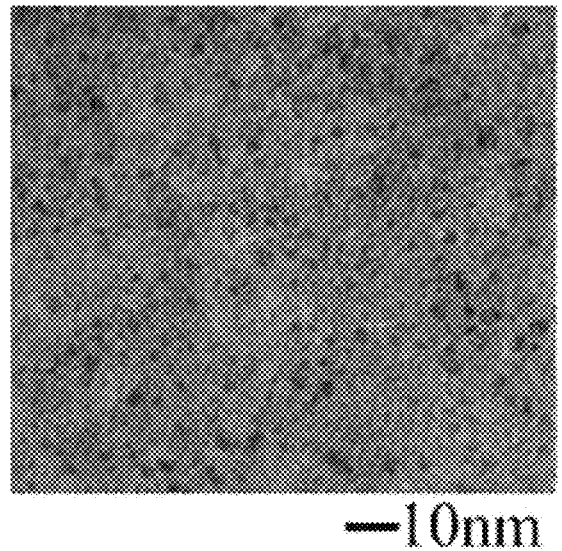
FIG. 3A shows a transmission electron microscope (TEM) photograph of a silica gel granular porous body obtained in Example 1 having a bimodal hierarchical porous structure supporting palladium, in which black dots indicate palladium nanoparticles.
Figure 3B:
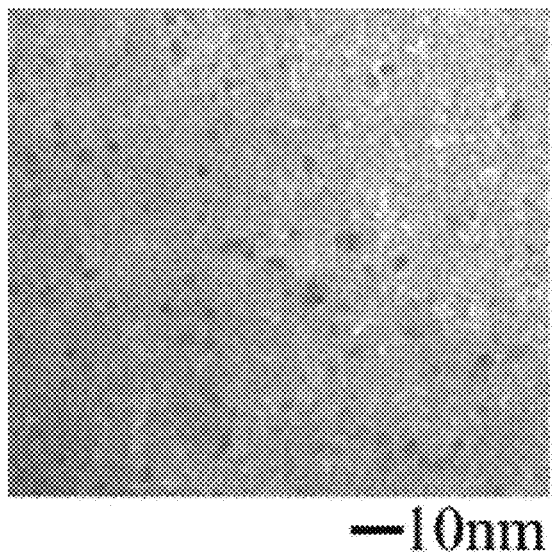
FIG. 3B shows a TEM photograph of a silica gel granular porous body obtained in Comparative Examples 2 not having a hierarchical porous structure supporting palladium, in which block dots indicate palladium nanoparticles. It shows that the silica gel granular porous body obtained in Example 1, which has the bimodal hierarchical porous structure supporting palladium, has more supporting amount of palladium nanoparticles than the silica gel granular porous body obtained in Comparative Example 2, which does not have the hierarchical porous structure supporting palladium.

In this specification, a numerical range indicated by using "to" indicates a range including numerical values described before and after "to" as the minimum value and the maximum value, respectively.

A catalyst of the present invention, in which metal is supported on an inorganic porous body having a hierarchical porous structure (hereinafter, also referred to as a "metal-supported catalyst of the present invention), and a method for producing the same will be described in detail.

1. Catalyst in Which Metal is Supported on Inorganic Porous Body Having Hierarchical Porous Structure The present invention is a catalyst in which metal is supported on an inorganic porous body having a hierarchical porous structure. The metal is supported 1) in a supercritical state or 2) in a polar organic solvent. The supporting of the metal is conducted 1) in a supercritical state or 2) in a polar organic solvent.

The catalyst of the present invention includes a carrier and a metal obtained by reducing a metal ion supported on the carrier 1) in a supercritical state or 2) in a polar organic solvent. In the present invention, the carrier is an inorganic porous body having a hierarchical porous structure. Note that the valence of the metal ion is not particularly limited in the present invention.

In the present invention, by causing the inorganic porous body having the hierarchical porous structure to support metal 1) in a supercritical state or 2) in a polar organic solvent, excellent catalytic activity can be exhibited even in a state of a low supporting amount of noble metal compared with those using a catalyst mainly containing Pd/C. Moreover, heat generation and spontaneous ignition are prevented because no organic porous body is used.

In the present invention, 1) in a supercritical state or 2) in a polar organic solvent, metal ions in a solution are once adsorbed to the inorganic porous body having the hierarchical porous structure and then reduced. Thus, metal nanoparticles can be uniformly dispersed into the inside of the skeleton with a diameter of several tens of μm or less, which constitutes the inorganic porous body having the hierarchical porous structure, to be supported without causing a density gradient of the metal nanoparticles in the diametrical direction of the skeleton. Therefore, the catalytic activity can be dramatically increased as compared with conventional catalysts.

In the present invention, the inorganic porous body having the hierarchical porous structure is an inorganic granular porous body having a hierarchical porous structure (hereinafter, also referred to as an inorganic granular porous body).

Each particle of the granular porous body has a skeleton body composed of an inorganic compound with a three-dimensional continuous network structure and further has a bimodal hierarchical porous structure composed of through-holes formed in voids of the skeleton body and pores extending from a surface to the inside of the skeleton body and dispersively formed on the surface.

In this specification, the "surface of the skeleton body" refers to a surface of the skeleton body exposed toward the through-hole, and does not include the inner wall surface of the pore formed in the skeleton body. In addition, the total surface of the skeleton body, which is the total of the "surface of the skeleton body" and the inner wall surface of the pore, is called "the surface of the inorganic granular porous body." The through-hole and the pore may also be referred to as a macropore and mesopore, respectively.

In the present invention, the inorganic compound that forms the skeleton body is assumed to be silica gel or silica glass ($SiO_2$). For each particle of the inorganic granular porous body, the most frequent pore diameter (nm) in the pore diameter distribution of the pores is preferably within a range of 2 nm or more and 80 nm or less, the most frequent pore diameter (μm) in the pore diameter distribution of the through-holes is preferably equal to or greater than five times the most frequent pore diameter (nm) of the pores and within arrange of 0.1 μm or more and 10 μm or less, and the particle diameter (μm) is preferably equal to or greater than five times the most frequent pore diameter (μm) of the through-holes and within a range of 20 μm or more and 250 μm or less.

The respective most frequent pore diameters of the through-holes and the pores are the most frequent values (mode values) in the pore diameter distributions measured by a well-known mercury press-in method. Note that one derived by a well-known BJH method based on nitrogen adsorption measurement may be used as the pore diameter distribution of the pores. In addition, the most frequent pore diameter of the through-holes is not much different from an average pore diameter derived as an average of the through-hole diameters measured at 20 to 30 arbitrary dispersed points in an electron micrograph of the skeleton body.

In the present invention, the inorganic granular porous body is created as follows: a massive silica monolithic porous body made of silica gel or silica glass with a three-dimensional continuous network-like structure is synthesized by a sol-gel method by spinodal decomposition described later in detail; and then the silica monolithic porous body is pulverized to be granulated before sintering or after sintering. In the present invention, since the particle diameter of each particle of the inorganic granular porous body immediately after the pulverization varies, the particles are sieved and classified so that the inorganic granular porous body with particles in a desired particle diameter range is obtained. Accordingly the upper limit value and the lower limit value of the above-described range of the particle diameter are the values of the openings of two types of sieves used for the classification process.

Next, a method for creating the inorganic granular porous body will be described. The method for creating the inorganic granular porous body is roughly classified into a synthesis step of a monolithic porous body having a bimodal hierarchical porous structure, which is a raw material of the inorganic granular porous body, and a subsequent granulation step.

First, the synthesis step of the monolithic porous body which is made of silica gel or silica glass ($SiO_2$) with a three-dimensional continuous network-like structure by a sol-gel method by spinodal decomposition will be described. The synthesis method is further divided into a sol preparation step, a gelation step and a removal step.

In the sol preparation step, a silica precursor as a raw material of silica gel or silica glass, and a coexisting substance serving to induce sol-gel transition and phase separation in parallel are added in an acid or alkaline aqueous solution, and at a low temperature of for example, 5° C. or lower at which sol-gel transition hardly proceeds, the mixture is stirred to cause a hydrolysis reaction, so that a uniform precursor sol is prepared.

As a main component of the silica precursor, water glass (sodium silicate aqueous solution), or an inorganic or organic silane compound can be used. Examples of the inorganic silane compound include tetraalkoxysilanes such as tetramethoxysilane, tetraethoxysilane, tetra-isopropoxysilane, tetra-n-butoxysilane and tetra-t-butoxysilane. Examples of the organic silane compound include trialkoxysilanes such as trimethoxysilane, triethoxysilane, triisopropoxysilane and triphenoxysilane, dialkoxysilanes such as methyldiethoxysilane, methyldimethoxysilane, ethyldiethoxysilane and ethyldimethoxysilane, monoalkoxysilanes such as dimethylethoxysilane and dimethylmethoxysilane, and the like, each of which has a substituent such as methyl, ethyl, propyl, butyl, hexyl, octyl, decyl, hexadecyl, octadecyl, dodecyl, phenyl, vinyl, hydroxyl, ether, epoxy, aldehyde, carboxyl, ester, thionyl, thio and amino. Alkoxysilicates containing a crosslinking reaction rate controlling group substituent such as a monoalkyl, a dialkyl and a phenyltriethoxy, oligomers such as a disilane being a dimer of the alkoxysilicate and a trisilane being a trimer of the alkoxysilicate, and the like are also considered as the silica precursors. Various compounds are commercially available as the hydrolyzable silane described above, and can be readily and inexpensively acquired, and it is easy to control a sol-gel reaction for forming a three-dimensional cross linked body including a silicon-oxygen bond.

The acid or alkaline aqueous solution is an aqueous solution in which an acid or a base functioning as a catalyst for promoting a hydrolysis reaction of a silica precursor is dissolved in water as a solvent. Specific examples of the acid include acetic acid, hydrochloric acid, sulfuric acid, nitric acid, formic acid, oxalic acid and citric acid, and specific examples of the base include sodium hydroxide, potassium hydroxide, aqueous ammonia, sodium carbonate, sodium hydrogen carbonate, amines such as trimethyl ammonium, ammonium hydroxides such as tert-butyl ammonium hydroxide, and alkali metal alkoxides such as sodium methoxide. Specific examples of the coexisting substance include polyethylene oxide, polypropylene oxide, polyacrylic acid, block copolymers such as polyethylene oxide polypropylene oxide block copolymers, cationic surfactants such as cetyltrimethylammonium chloride, anionic surfactants such as sodium dodecyl sulfate, and nonionic surfactants such as polyoxyethylene alkyl ethers. Water is used as a solvent, but an alcohol such as methanol or ethanol may be used.

In the gelation step, the precursor sol prepared in the sol preparation step is injected into a gelation container, and gelled at a temperature of, for example, about 40° C. at which sol-gel transition easily proceeds. Here, in the precursor sol, a coexisting substance serving to induce sol-gel transition and phase separation in parallel is added, and therefore spinodal decomposition is induced to gradually form a co-continuous structure of a silica hydrogel (wet gel) phase and a solvent phase which has a three-dimensional continuous network-like structure.

In the gelation step, a polycondensation reaction of the wet gel slowly progresses to cause shrinkage of the gel even after the silica hydrogel phase is formed, and therefore, as a step subsequent to the gelation step (gelation subsequent step), the co-continuous structure of the silica hydrogel phase and the solvent phase which is formed in the hole of a sol accommodation body in the gelation step is immersed in a basic aqueous solution such as aqueous ammonia, and subjected to a heating treatment in a pressurized container to further promote the hydrolysis reaction, the polycondensation reaction and a dissolution and reprecipitation reaction of the silica hydrogel phase, so that the skeleton structure of the silica hydrogel phase can be further strengthened. The step subsequent to the gelation step may be carrier out as necessary. The heating treatment is not necessarily required to be performed in a pressurized container or a closed container, but since an ammonia component or the like may be generated or volatilized by heating, it is preferable to perform the heating treatment in a closed container or a container having pressure resistance.

As the dissolution and reprecipitation reaction of silica fine particles forming the skeleton body of the silica hydrogel phase proceeds, the pore diameter of pore formed in the skeleton body is increased. Further, when the dissolution and reprecipitation reaction is repeated in hydrothermal treatment, it is possible to perform control to further increase the pore diameter. The control of the pore diameter can also be performed by adding urea in the precursor sol besides a catalyst and a coexisting substance. Urea is hydrolyzed at a temperature of 60° C. or higher to produce ammonia, and the pore diameter of the pore formed in the skeleton body of the wet gel synthesized in the gelation step is increased by the ammonia. Thus, it is possible to control the pore diameter by adding urea. On the other hand, control of the structure and pore diameter of the through-hole is made possible by adjusting the amount of water or the silica precursor added to the precursor sol in the sol preparation step, or the composition and addition amount of the coexisting substance.

Subsequently, in the removal step, washing and drying, or only drying of the wet gel is performed to remove the solvent phase containing additives, unreacted substances and the like. The space after removal of the solvent phase forms a through-hole. By washing, a surface tension during drying which is caused by additives, unreacted substances and the like remaining in the solvent phase can be eliminated to suppress distortion and cracking in the gel during drying. A washing liquid is desirably a liquid such as an organic solvent or an aqueous solution A liquid in which an organic compound or an inorganic compound is dissolved can also be used. Further, even if a solution having a pH different from the isoelectric point of the gel, such as an acid or an alkali, is used as the washing liquid, additives and the like remaining in the gel can be easily removed. Specifically, various kinds of acids such as hydrochloric acid, sulfuric acid, nitric acid, hydrofluoric acid, acetic acid, formic acid, carbonic acid, citric acid and phosphoric acid, and various kinds of bases such as sodium hydroxide, potassium hydroxide, ammonia, water-soluble amine, sodium carbonate and sodium hydrogen carbonate can be used. For drying the wet gel, natural drying may be adopted, and for eliminating distortion and cracks generated in drying of the wet gel, it is also preferable to adopt drying that is performed after replacement of a solvent in the wet gel by a solvent having a low surface tension lower than that of water, such as isopropanol, acetone, hexane and hydrofluorocarbon drying by freezing and sublimation; supercritical drying that is performed in a non-surface-tension state after exchange of a solvent in the wet gel with supercritical carbon dioxide; or the like.

Subsequently, the resulting dried gel can be sintered by firing to obtain silica glass. When the firing temperature is lower than the glass transition temperature (about 1000° C.) of silica, silica glass is not formed.

By passing through the above sol preparation step, gelation step and removal step, a monolithic porous body of dried silica gel or silica glass of three-dimensional continuous network-like structure which has a bimodal hierarchical porous structure is obtained.

The granulation step is a step of crushing and granulating the massive monolithic porous body obtained through the sol preparation step, the gelation step and the removal step described above. The pulverization process in the granulation step may be performed using a human hand, a mortar or the like, or a crushing device such as a ball mill. Moreover, in a case where the dried gel obtained in the removal step is sintered, the granulation step may be performed before or after the sintering.

The granulated monolithic porous body after the granulation step is sieved and classified by sieves with openings of X μm and Y μm (where $D0 \leq X < Y \leq 1000$) to be recovered as an inorganic granular porous body with a particle diameter Dp within a desired particle diameter range (D 0 μm or more and 1000 μm or less). However, the lower limit value D0 (μm) of the desired particle diameter range is a greater value of either 20 (μm) or five times the most frequent pore diameter (μm) in the pore diameter distribution of the through-holes.

In the present invention, each of the pore diameter, the through-hole diameter and the particle diameter can be independently controlled. However, the reason that the most frequent pore diameter (μm) in the pore diameter distribution of the through-holes is defined as being equal to or greater than five times the most frequent pore diameter (nm) in the pore diameter distribution of the pores and the particle diameter (μm) is defined as being equal to or greater than five times the most frequent pore diameter (μm) in the pore diameter distribution of the through-holes is based on empirical knowledge that a dimensional ratio of at least about five times is necessary for both between the pore diameter and the through-hole diameter and between the through-hole diameter and the particle diameter in order for the skeleton body of each particle of the inorganic granular porous body to maintain a three-dimensional continuous network structure of a bimodal hierarchical porous structure even after the granulation.

All the inorganic granular porous bodies used in the respective Examples are silica gel inorganic granular porous bodies created by the above-described creation method, that is, through the synthesis step by the sol-gel method by spinodal decomposition of the monolithic porous body and the granulation step.

More specifically, the inorganic granular porous body used in each Example was created in the following manner. In 10 mL (milliliter, cm$^3$) of 0.01 mol/L acetic acid aqueous solution, 0.9 g of polyethylene glycol (molecular weight: 10,000) as a coexisting substance was dissolved, and 5 mL of tetramethoxysilane (TMOS, silica precursor) was added. The mixture was stirred to obtain homogeneous solution. Thereafter the solution was gelled at 40° C. Thereafter, the gel was dipped in 0.1 M aqueous ammonia, heated at 100° C. for 24 hours in a closed container, and then sintered at 600° C. for five hours. The resulting silica monolithic porous body was pulverized in a mortar, and classified using a JIS standard sieve so as to be in a predetermined particle diameter range for each Example. Then, a silica inorganic granular porous body was obtained. In each Example, the through-hole diameter was controlled by increasing or decreasing the amount of polyethylene glycol added, and the pore diameter was controlled by adjusting the temperature and time for heating with 0.1 M aqueous ammonia.

Silica (silica gel or silica glass) was assumed as the inorganic compound constituting the skeleton body of the inorganic granular porous body, but the inorganic compound is not limited to silica. Examples of the inorganic compound besides silica include oxides and nitrides containing a typical metal element or a transition metal element, such as titania ($TiO_2$), alumina ($Al_2O_3$), zirconia ($ZrO_2$), hafnia ($HfO_2$), germanium oxide ($GeO_2$), silicon nitride (SiN), alumina nitride (AlN) or gallium nitride (GaN); oxides and nitrides containing an alkali metal element and an alkaline earth metal element such as lithium (Li), sodium (Na), potassium (K), rubidium (Rb), cesium (Cs), beryllium (Be), magnesium (Mg), calcium (Ca), strontium (Sr) and barium (Ba); complexes of these oxides and nitrides containing a typical element such as boron (B), carbon (C), phosphorus (P) or sulfur (S). Moreover, the inorganic compound besides these may be an organic-inorganic hybrid compound such as silicone represented by the chemical formula of $(OSi(CH_3)_2)_n$, and it is desirable that the inorganic compound constituting the skeleton body of the inorganic granular porous body be not decomposed by reaction.

In the present invention, silica and titania are particularly preferable as the inorganic compounds constituting the skeleton body of the inorganic granular porous body.

An example of a method for synthesizing a titania monolithic porous body before the granulation when the skeleton body of the inorganic granular porous body is titania ($TiO_2$) will be briefly described.

To a mixed solution of 2.5 mL of 1-propanol and 2.5 mL of ethyl acetoacetate containing 0.4 g of polyethylene glycol (average molecular weight: 10,000), 5.0 mL of tetra-n-propyl titanate is added, and then 1.0 mL of 1 mol/L ammonium nitrate aqueous solution is added while stirring to obtain homogeneous solution. Then, the homogeneous solution was transferred to a closed container and left at 40° C. for one day to gel. The resulting gel is dipped in a mixed solvent of water and ethanol for one day, washed, air-dried, and sintered at 500° C. for five hours to obtain a titania monolithic porous body.

When the inorganic compound constituting the skeleton body is titania, acid resistance and alkali resistance are better than those of silica. Silica dissolves in an aqueous solution at pH 2 or less or pH 11 or more, whereas titania can be used without dissolving.

In the present invention, the specific surface area of the inorganic porous body having a hierarchical porous structure is preferably 50 to 1600 m$^2$/g or less, more preferably 200 to 1000 m$^2$/g, still more preferably 250 to 600 m$^2$/g in a BET specific surface area from the viewpoint of supporting metal in the pores of the inorganic porous body.

In the present invention, the particle diameter of the inorganic porous body having a hierarchical porous structure is preferably 5 to 1000 μm, more preferably 10 to 300 μm, still more preferably 20 to 100 μm from the viewpoint of supporting metal in the pores of the inorganic porous body.

In the present invention, the through-hole diameter of the inorganic porous body having a hierarchical porous structure is preferably 0.1 to 50 μm, more preferably 0.1 to 20 μm, still more preferably 0.1 to 10 μm from the viewpoint of supporting metal in the pores of the inorganic porous body.

In the present invention, the pore diameter (the mode value in the pore diameter distribution) of the inorganic porous body having a hierarchical porous structure is preferably 2 to 200 nm, more preferably 2 to 80 nm, still more preferably 2 to 30 nm from the viewpoint of supporting metal in the pores of the inorganic porous body.

In the above embodiment, since the inorganic porous body having a hierarchical porous structure has a bimodal hierarchical porous structure composed of the through-holes and pores, assumed is a case where the monolithic porous body in the process of creating the inorganic granular porous body also has a similar bimodal hierarchical porous structure. However, the monolithic porous body before the granulation may have a three-step hierarchical porous structure having holes with a greater pore diameter than the through holes, in addition to the through-holes and the pores. In this case, when the monolithic porous body is pulverized and granulated to create an inorganic granular porous body, the skeleton body is pulverized along the holes. Thus, in the process of forming the holes, the diameter of the skeleton body enclosed by the holes are made uniform to some extent so that the particle diameter Dp of the inorganic granular porous body after the pulverization can be efficiently adjusted within a certain range.

In the present invention, from the viewpoint of enhancing the catalytic activity the above-described 2) polar organic solvent is preferably at least one polar organic solvent selected from the group consisting of methanol, acetonitrile, acetone, 2-propanol and tetrahydrofuran. In the present invention, from the viewpoint of further enhancing the catalytic activity, the above-described 2) polar organic solvent is preferably methanol and/or acetonitrile in particular.

In the present invention, from the viewpoint of enhancing the catalytic activity, the metal is preferably a platinum group element and/or a group 10 element.

Examples of the platinum group element include ruthenium (Ru), rhodium (Rh), palladium (Pd), osmium (Os), iridium (Ir) and platinum (Pt), and examples of the group 10 element include nickel (Ni), palladium and platinum. Among these, platinum and palladium are more preferable, and palladium is still more preferable so that the catalytic activity can be further enhanced.

In the present invention, the supporting amount of metal is preferably 0.01 to 30 wt % based on 100 wt % of the metal-supported catalyst.

In the present invention, from the viewpoint of enhancing the catalytic activity, the supporting amount of metal supported 1) in the supercritical state is usually 0.01 to 6 wt %, preferably 0.1 to 5.5 w/%, more preferably 0.2 to 5 wt %, still more preferably 0.3 to 4.75 wt %, particularly preferably 0.5 to 4.5 wt % based on 100 wt % of the metal-supported catalyst.

In the present invention, from the viewpoint of enhancing the catalytic activity; the supporting amount of metal supported 1) in the supercritical state is usually 0.01 wt % or more, preferably 0.1 wt % or more, more preferably 0.2 wt % or more, still more preferably 0.3 wt % or more, particularly preferably 0.5 wt % or more based on 100 wt % of the metal-supported catalyst.

In the present invention, from the viewpoint of enhancing the catalytic activity, the supporting amount of metal supported 1) in the supercritical state is usually 6 wt % or less, preferably 5.5 wt % or less, more preferably 5 wt % or less, still more preferably 4.75 wt % or less, particularly preferably 4.5 wt % or less based on 100 wt % of the metal-supported catalyst.

In the present invention, from the viewpoint of enhancing the catalytic activity, the supporting amount of metal supported 2) in the polar organic solvent is usually 0.01 to 30 wt %, preferably 0.1 to 25 wt %, more preferably 0.5 to 20 wt %, still more preferably 0.75 to 15 wt %, particularly preferably 1 to 10 wt % based on 100 wt % of the metal-supported catalyst.

In the present invention, from the viewpoint of enhancing the catalytic activity, the supporting amount of metal supported 2) in the polar organic solvent is usually 0.01 wt % or more, preferably 0.1 wt % or more, more preferably 0.5 wt % or more, still more preferably 0.75 wt % or more, particularly preferably 1 wt % or more based on 100 wt % of the metal-supported catalyst.

In the present invention, from the viewpoint of enhancing the catalytic activity, the supporting amount of metal supported 2) in the polar organic solvent is usually 30 wt % or less, preferably 25 wt % or less, more preferably 20 wt % or less, still more preferably 15 wt % or less, particularly preferably 10 wt % or less based on 100 wt % of the metal-supported catalyst.

The metal-supported catalyst of the present invention exhibits excellent catalytic activity in various organic reactions.

The organic reactions using the metal-supported catalyst of the present invention as a catalyst are not particularly limited. Examples of the organic reactions using the metal-supported catalyst of the present invention as a catalyst include catalytic reaction of general hydrogenation such as catalytic reaction including dehydrogenation or oxidation reaction, deprotection reaction by hydrogenation of a benzyl group or a benzyloxycarbonyl group, and substitution reaction of hydrogen for a halogen atom (chlorine, bromine, iodine or the like) on an aromatic ring, or coupling reactions.

The metal-supported catalyst of the present invention is preferably used as a reduction catalyst Reduction Reaction The metal-supported catalyst of the present invention can be used in reduction reactions as a heterogeneous catalyst Hydrogenation reaction, which is one of the reduction reactions, is a reaction in which a reactant is hydrogenated and reduced by bringing a hydrogen source into contact with the reactant under the presence of the metal-supported catalyst of the present invention.

Examples of the hydrogen source include: reducing gases such as hydrogen, carbon monoxide and ethylene; alcohols such as methanol, ethanol and propanol; hydrazines such as hydrazine methylhydrazine, allylhydrazine and phenylhydrazine, derivatives thereof and salts thereof-carboxylic acids such as formic acid; and the like. Among these, hydrogen and hydrazine are preferable from the viewpoint of enhancing the catalytic activity.

The used amount of hydrogen source is preferably equal to or greater than one time the reactant in mole, more preferably equal to or greater than five times the reactant in mole since the amount of hydrogen source leads to high reaction efficiency and a short reaction time.

The used amount of hydrogen source is preferably equal to or less than ten times the reactant in mole, more preferably equal to or less than 100 times the reactant in mole since the amount of hydrogen source leads to high reaction efficiency and a short reaction time.

The method for introducing the hydrogen source into the reaction system is not particularly limited. When the hydrogen source is hydrogen, it is preferable to introduce hydrogen into the reaction system under normal pressure or in a pressurized state. When the hydrogen source is hydrazine, it is preferable to introduce an aqueous solution thereof into the reaction system.

The reactant is a compound having a functional group or moiety to be reduced, and is not particularly limited. Examples thereof includes: a compound having an unsaturated bond such as a carbon-carbon double bond or triple bond; a compound having a nitro group; a compound having an ester group; a compound having a carboxyl group; a compound having a carbonyl group (ketone, aldehyde group) adjacent to an aromatic ring; a compound having an alkoxy group such as benzyloxy; a compound having an ether group such as benzyl ether, a heterocyclic compound such as furan or pyrrole an organic nitrogen compound having an acetyl group, a carbonyl group, an imide group, an imine group, an azo group, a diazo group or the like; and the like. More specifically, preferable examples of the reactant include an aromatic nitro compound, an aromatic benzyl ester compound, an aromatic benzyl ether compound, a halogen atom on an aromatic ring, alkyne, alkene and the like. These respective compounds are converted into an aromatic amino compound, a compound having a carboxyl group, a compound having a hydroxyl group, an aromatic hydrocarbon compound, a compound having an amino group, and alkane by reduction reaction. Moreover, a substituent in the reactant may include an alkyl group, an aromatic ring, or the like as a substituent resistant to reduction. In this specification, a halogen atom on an aromatic ring means a substituent in which chlorine, bromine or iodine is substituted for at least one hydrogen atom of the aromatic ring.

For example, the following compounds can be used as the reactant

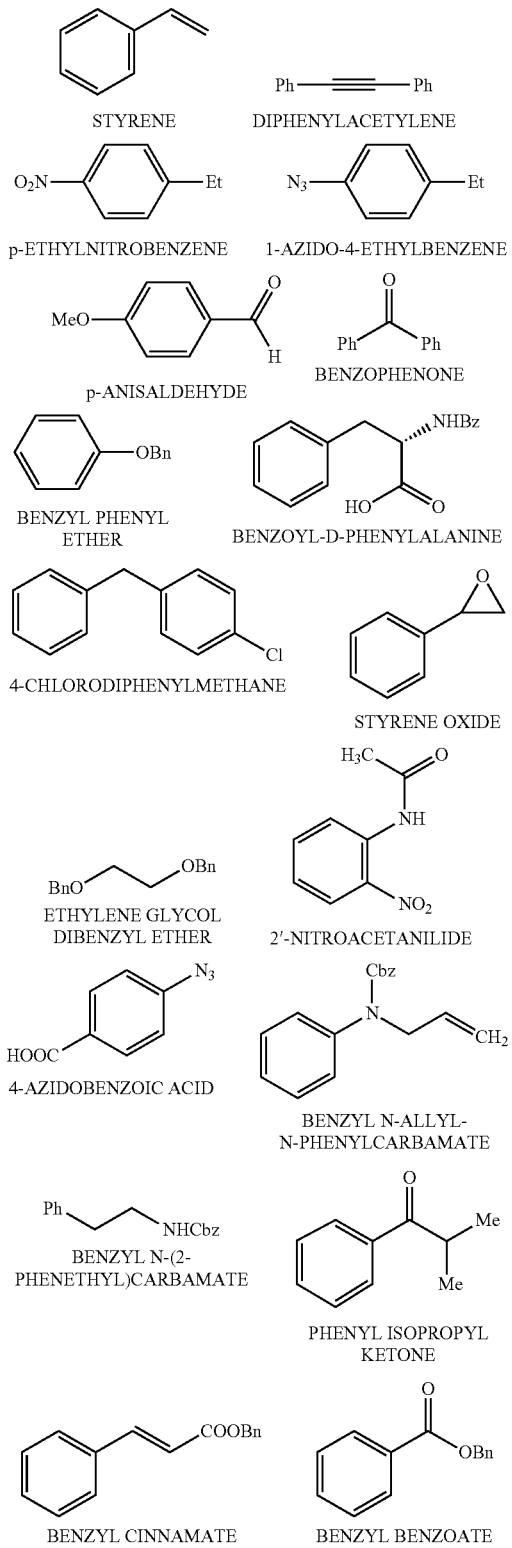

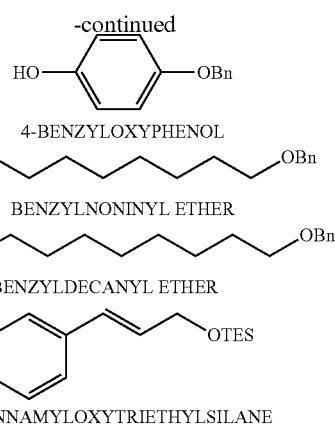

In the above reactants, Ph means a phenyl group, Et means an ethyl group, Me means a methyl group, Bn means a benzyl group, Bz means a benzoyl group, Cbz means a benzyloxycarbonyl group, and TES means a triethylsilyl group.

To determine the selectivity of the reduction reaction for the above reactants, it is preferable to select a functional group having alkyne, alkene, azide, nitro, aromatic N-Cbz, aliphatic N-Cbz aromatic ketone, benzyl ester, a halogen atom on an aromatic ring, aromatic benzyl ether aromatic epoxide, aliphatic benzyl ether, aromatic aldehyde or O-TES and exhaustively investigate the reduction activity. In the above notation of the substrates, N means a nitrogen atom, and O means an oxygen atom.

The metal-supported catalyst of the present invention is preferably used as a reduction catalyst for hydrogenating the above reactants.

In the above-described reduction reaction, the used amount of metal-supported catalyst of the present invention is usually 0.001 to 3 mol %, preferably 0.005 to 2.5 mol %, more preferably 0.007 to 2 mol %, still more preferably 0.01 to 1.5 mol %, particularly preferably 0.012 to 1.2 mol % in supported metal conversion based on one mole of the reactant from the viewpoint of enhancing the catalytic activity:

The reduction reaction is preferably performed in a solvent. Examples of the solvent include: water alcohols such as methanol, ethanol, propanol and butanol; ethers such as diethyl ether, dimethoxymethane, dimethoxyethane, tetrahydrofuran (ThF) and cyclopentyl methyl ether, acetone; acetonitrile; dimethylformamide; polar solvents such as dimethyl sulfoxide; and the like. These solvents may be used alone or in combination of two or more. Among these, methanol is particularly preferable from the viewpoint of controlling the selectivity of the reduction reaction.

The reaction conditions for the reduction reaction are not particularly limited, but the reaction temperature is preferably 0° C. to 200° C., more preferably 20 to 135° C. The reaction time is preferably ten minutes to 72 hours, more preferably 30 minutes to 24 hours. The reaction pressure is preferably normal pressure to 20 MPa, more preferably normal pressure to 10 MPa.

2. Method for Producing Catalyst in Which Metal is Supported on Inorganic Porous Body Having Hierarchical Porous Structure A method for producing the metal-supported catalyst of the present invention is a method for producing a catalyst in which metal is supported on an inorganic porous body having a hierarchical porous structure, the method including a step of causing the inorganic porous body to support the metal 1) in a supercritical state or 2) in a polar organic solvent.

The catalyst of the present invention in which metal is supported on an inorganic porous body having a hierarchical porous structure is produced by causing the inorganic porous body to support the metal. The supporting of the metal is conducted 1) in a supercritical state or 2) in a polar organic solvent.

The method for producing the catalyst of the present invention includes the steps of: causing an inorganic porous body having a hierarchical porous structure to support a metal ion 1) in a supercritical state or 2) in a polar organic solvent and reducing the metal ion.

In the present invention, from the viewpoint of enhancing the catalytic activity; the above-described 2) polar organic solvent is preferably at least one polar organic solvent selected from the group consisting of methanol, acetonitrile, acetone, 2-propanol ad tetrahydrofuran. In the present invention, from the viewpoint of further enhancing the catalytic activity the above-described 2) polar organic solvent is preferably methanol and/or acetonitrile in particular.

In the present invention, from the viewpoint of enhancing the catalytic activity the metal supported on the inorganic porous body having a hierarchical porous structure is preferably a platinum group element and/or a group 10 element.

Examples of the platinum group element include ruthenium (Ru), rhodium (Rh), palladium (Pd), osmium (Os), iridium (Ir) and platinum (Pt), and examples of the group 10 element include nickel (Ni), palladium and platinum. Among these, platinum and palladium are more preferable, and palladium is still more preferable, from the viewpoint of further enhancing the catalytic activity.

In the present invention, the supporting amount of metal is preferably 0.01 to 30 wt % based on 100 wt % of the metal-supported catalyst.

From the viewpoint of enhancing the catalytic activity, the supporting amount of metal supported 1) in the supercritical state is usually 0.01 to 6 wt %, preferably 0.1 to 5.5 wt %, more preferably 0.2 to 5 wt %, still more preferably 0.3 to 4.75 wt %, particularly preferably 0.5 to 4.5 wt % based on 100 wt % of the metal-supported catalyst.

From the viewpoint of enhancing the catalytic activity, the supporting amount of metal supported 1) in the supercritical state is usually 0.01 wt % or more, preferably 0.1 w % or more, more preferably 0.2 wt % or more, still more preferably 0.3 wt % or more, particularly preferably 0.5 wt % or more based on 100 wt % of the metal-supported catalyst.

From the viewpoint of enhancing the catalytic activity, the supporting amount of metal supported 1) in the supercritical state is usually 6 wt % or less, preferably 5.5 wt/o or less, more preferably 5 wt % or less, still more preferably 4.75 wt % or less, particularly preferably 4.5 wt % or less based on 100 wt %/o of the metal-supported catalyst.

From the viewpoint of enhancing the catalytic activity, the supporting amount of metal supported 2) in the polar organic solvent is usually 0.01 to 30 wt %, preferably 0.1 to 25 wt %, more preferably 0.5 to 20 wt %, still more preferably 0.75 to 15 wt %, particularly preferably 1 to 10%/o based on 100 wt % of the metal-supported catalyst.

From the viewpoint of enhancing the catalytic activity, the supporting amount of metal supported 2) in the polar organic solvent is usually 0.01 wt % or more, preferably 0.1 wt % or more, more preferably 0.5 wt % or more, still more preferably 0.75 wt % or more, particularly preferably 1 wt % or more based on 100 wt % of the metal-supported catalyst.

From the viewpoint of enhancing the catalytic activity, the supporting amount of metal supported 2) in the polar organic solvent is usually 30 wt % or less, preferably 25 wt % or less, more preferably 20 wt % or less, still more preferably 15 wt % or less, particularly preferably 10 wt % or less based on 100 wt % of the metal-supported catalyst.

In the present invention, the method for performing the supporting (immobilization) of the metal 1) in the supercritical state preferably includes a step of preparing metal precursor fluid by dissolving a metal precursor in supercritical fluid (preparation step A), a step of impregnating (contacting) an inorganic porous body having a hierarchical porous structure with the metal precursor fluid (impregnation step A), and a step of reducing the inorganic porous body having the hierarchical porous structure (reduction step). Hereinafter, each step will be described.

In this specification, the supercritical state is a state of a substance at a temperature and a pressure equal to or higher than a critical point. The supercritical fluid refers to a fluid in the supercritical state, and the fluid in this state is a substance having dissolving ability equivalent to that of liquid, diffusivity nearly equal to that of gas, and viscosity. Therefore, a large amount of metal precursors can be easily and quickly transported into the pores of the inorganic porous body having the hierarchical porous structure.

Preparation Step A

In the preparation step A, a metal precursor fluid is prepared by dissolving a metal precursor in a supercritical fluid.

Examples of the metal precursor include metal and/or metalloid alkoxide, metal and/or metalloid acetylacetonate, metal and/or metalloid organic acid salt, metal and/or metalloid nitrate, metal and/or metalloid oxychloride and metal and/or metalloid chloride. In the present invention, the metal of the metal precursor is preferably a platinum group element and/or a group 10 element. In the present invention, palladium acetate is particularly preferable as the metal precursor. In the preparation step A, the metal precursor may be used alone or in a combination of two or more.

For example, as the supercritical fluid, hydrocarbon such as methane, ethane, propane, butane, ethylene and propylene; alcohols such as methanol, ethanol, n-propanol, iso-propanol, n-butanol, iso-butanol, sec-butanol and tert-butanol; ketones such as acetone and methyl ethyl ketone; carbon dioxide, water, ammonia, chlorine, chloroform, freon and the like can be used. Among them, carbon dioxide is preferable because of its mild critical conditions, incombustibility, non-toxicity and inexpensiveness.

When carbon dioxide is used as the supercritical fluid, alcohols such as methanol, ethanol and propanol, ketones such as acetone and methyl ethyl ketone, and aromatic hydrocarbons such as benzene, toluene and xylene, and the like can be used as entrainers in order to adjust the solubility of the metal precursor in carbon dioxide.

Impregnation Step A

In the impregnation step A, the inorganic porous body having the hierarchical porous structure is impregnated (contacted) with the metal precursor fluid.

The pressure and temperature for impregnating the inorganic porous body having the hierarchical porous structure with the metal precursor fluid prepared by dissolving the metal precursor in the supercritical fluid are employed as appropriate within a range of pressure and temperature at which a supercritical state is reached. For example, in a case of supercritical carbon dioxide, the temperature is selected in a range of 31.1 to 100° C., and the pressure at which the supercritical state is reached at the selected temperature is selected as the pressure. For example, conditions of 31.1 to 60° C. and 7.38 to 15 MPa are employed.

The time for impregnating the inorganic porous body having the hierarchical porous structure with the metal precursor fluid prepared by dissolving the metal precursor in the supercritical fluid should be sufficient time for the supercritical fluid to permeate the pores within the inorganic porous body having the hierarchical porous structure. Such time is usually 1 to 24 hours.

Reduction Step

In the reduction step, the reduction reaction can progress by heating while flowing hydrogen gas or mixed gas of hydrogen gas and inert gas such as nitrogen or argon through the inorganic porous body having the hierarchical porous structure which the supercritical fluid has penetrated. The flow rate at which the gas flows is preferably 5 mL/min to 20 mL/min. To promote the reduction reaction, the heating can be performed within a range of 100° C. to 500° C. for three to eight hours.

In the present invention, the method for performing the supporting of the metal 2) in the polar organic solvent preferably includes a step of preparing metal precursor solution by dissolving a metal precursor in the polar organic solvent (preparation step B), a step of impregnating (contacting) an inorganic porous body having a hierarchical porous structure with the metal precursor solution (impregnation step B), a step of reducing the inorganic porous body having the hierarchical porous structure by a reducing agent (reduction step), and a step of removing the reducing agent (reducing agent removal step). The above-described reduction step and reducing agent removal step may be combined with the step of reducing the inorganic porous body having the hierarchical porous structure (reduction step), which is described in the method for performing the supporting (immobilization) of the metal 1) in the supercritical state Hereinafter each step will be described.

Preparation Step B

In the preparation step B, a metal precursor solution is prepared by dissolving a metal precursor in the polar organic solvent.

As the metal precursor for example, metal and/or metalloid alkoxide, metal and/or metalloid acetylacetonate, metal and/or metalloid organic acid salt, metal and/or metalloid nitrate, metal and/or metalloid oxychloride, metal and/or metalloid chloride, and the like can be used alone, or the mixture of two or more of these can be used. In the present invention, the metal of the metal precursor is preferably a platinum group element and/or a group 10 element. In the present invention, palladium acetate is particularly preferable as the metal precursor. In the preparation step B, the metal precursor may be used alone or in a combination of two or more.

Examples of the polar organic solvent include protic polar solvents such as an alcohol-based solvent and a solvent having carboxylic acid, and aprotic polar solvents such as a ketone-based solvent and an ether-based solvent Among these, acetonitrile, acetone, tetrahydrofuran, 1,4-dioxane, methyl ethyl ketone, acetic acid, formic acid, dimethylformamide, dimethylsulfoxide and alcohols having one to four carbon atoms are preferable so that the reduction reactivity can be enhanced for the catalyst. Examples of the alcohols having one to four carbon atoms include methanol, ethanol, l-propanol 2-propanol, 1-butanol, 2-butanol, isobutanol and t-butanol. In the present invention, methanol and/or acetonitrile are particularly preferable as the polar organic solvents so that the reduction reactivity can be further enhanced for the catalyst. In the preparation step B, the above-mentioned polar organic solvents may be used alone or in a combination of two or more.

Impregnation Step B

In the impregnation step B, the inorganic porous body having the hierarchical porous structure is impregnated (contacted) with the metal precursor solution.

The temperature for impregnating (contacting) the inorganic porous body having the hierarchical porous structure with the metal precursor solution in which the metal precursor is dissolved is selected as appropriate from a wide range. Such temperature is usually 10 to 60° C.

The time for impregnating (contacting) the inorganic porous body having the hierarchical porous structure with the metal precursor solution in which the metal precursor is dissolved should be sufficient time for the metal precursor solution to permeate the pores within the inorganic porous body having the hierarchical porous structure. Such time is usually 0.5 to 24 hours.

Reduction Step

In the reduction step, the inorganic porous body having the hierarchical porous structure impregnated with the metal precursor solution is reduced by a reducing agent.

Examples of the reducing agent include hydrazine ($N_2H_4$) and hydrates of hydrazine ($N_2H_4 \cdot nH_2O$) such as hydrazine monohydrate; alcohols such as methanol and ethanol; and reducing sugars such as glucose.

In the reduction step, the inorganic porous body having the hierarchical porous structure impregnated with the metal precursor solution is allowed to react in the reducing agent solution at room temperature and under normal pressure for 1 to 24 hours to promote the reduction reaction.

Reducing Agent Removal Step

In the reducing agent removal step, the reducing agent is removed after performing the reduction step.

Examples of the method for removing the reducing agent include a filtration method. The method for removing the reducing agent is preferably selected as appropriate according to the type of reducing agent used. Examples of the filtration method include a method for filtering the supernatant after centrifugation, and a direct filtration method.

Example

Hereinafter, the present invention will be described specifically with reference to Examples and Comparative Examples. However, the present invention is not limited to Examples.

Production Example 1 of Silica Gel Granular Porous Body Having Bimodal Hierarchical Porous Structure In 10 milliliters (mL) of 0.01 M (molarity) acetic acid aqueous solution, 0.8 grams (g) of polyethylene glycol (molecular weight 10,000) and 0.2 g of urea, which are coexisting substances, were dissolved, and 5 mL of tetramethyl orthosilicate (tetramethoxysilane, silica precursor) was added. The mixture was stirred for 30 minutes under ice cooling to obtain homogeneous solution, and a precursor sol was obtained (sol preparation step). A melamine sponge (3×3×5 cm square block, manufactured by BASF) was provided as a sol accommodation body, and the resulting precursor sol was absorbed by the melamine sponge. The melamine sponge was accommodated in a polyethylene plastic bag, and the bag was sealed and dipped in a hot water bath set at 40° C. to be heated for gelation. The resulting wet gel was placed in a closed container and subjected heat treatment at 100° C. for 18 hours. Thereafter, the wet gel was immersed in one liter (L) of water and washed. The washed wet gel was air-dried. The resulting dried gel was sintered at 650° C. for five hours to remove the melamine sponge, and then a massive silica gel porous body having a bimodal hierarchical porous structure was obtained. The massive silica gel porous body was crushed lightly using a mortar to obtain a silica gel granular porous body having a bimodal hierarchical porous structure.

The resulting silica gel granular porous body having the bimodal hierarchical porous structure had the particle diameter of 20/63 μm, the through-hole diameter of 0.5 to 1.0 μm, and the average pore diameter of the pores of 4 nm. The particle diameter was determined using a JIS standard sieve, the through-hole diameter was determined from the void of the skeleton formed by silica gel in a scanning electron microscope (SEM) photographic image, and the average pore diameter of the pores was determined by a BJH method based on nitrogen adsorption measurement. Moreover, the pore diameter distribution and the specific surface area of the silica gel granular porous body having the bimodal hierarchical porous structure were measured by a nitrogen adsorption/desorption method, and the specific surface area was 591 m$^2$/g as calculated by the BJH method.

Production Example 2 of Silica Gel Granular Porous Body Having Bimodal Hierarchical Porous Structure A silica gel granular porous body having a bimodal hierarchical porous structure was obtained as in Production Example 1, except that "the wet gel was placed in a closed container and subjected to heat treatment at 100° C. for 18 hours" in the method described in Production Example 1 was replaced with "the wet gel was placed in a closed container, dipped in 0.1 M ammonia aqueous solution, and subjected to heat treatment at 60° C. for 18 hours." The resulting silica gel granular porous body having the bimodal hierarchical porous structure had the particle diameter of 20/63 μm, the through-hole diameter of 0.5 to 1.0 μm, the average pore diameter of the pores of 12 nm, and the specific surface area of 499 mg.

Production Example 3 of Silica Gel Granular Porous Body Having Bimodal Hierarchical Porous Structure A silica gel granular porous body having a bimodal hierarchical porous structure was obtained as in Production Example 1, except that "the wet gel was placed in a closed container and subjected to heat treatment at 100° C. for 18 hours" in the method described in Production Example 1 was replaced with "the wet gel was placed in a closed container, dipped in 0.1 M ammonia aqueous solution, and subjected to heat treatment at 10° C. for 18 hours." The resulting silica gel granular porous body having the bimodal hierarchical porous structure had the particle diameter of 20/63 μm, the through-hole diameter of 0.5 to 1.0 μm, the average pore diameter of the pores of 25 nm, and the specific surface area of 282 m$^2$/g.

Example 1

Supercritical Method for Supporting Palladium

A palladium solution was prepared by dissolving 0.05 g of palladium acetate in 20 mL of acetone and placed in a stainless steel pressure-resistant container together with 0.5 g of the silica gel granular porous body having the bimodal hierarchical porous structure obtained in Production Example 1, and the container was closed. Then, carbon dioxide gas was injected at 60° C. into the stainless steel pressure-resistant container until the pressure reached 20 megapascals (MPa). Thereafter, the inside of the container was stirred using a magnetic stirrer from the outside of the stainless steel pressure-resistant container, and the conditions of 60° C. and 20 MPa were maintained for 24 hours. Thereafter, the pressure in the reaction container was returned to normal pressure over 30 minutes, and the remaining acetone was removed by evaporation under reduced pressure. The dried reactant was placed in a glass tube, and a mixed gas of hydrogen and nitrogen was continuously flowed at a flow rate of 10 mL/min to heat and reduce the reactant at 200° C. for five hours from the outer side of the glass tube. Then, a catalyst, in which palladium was supported on the silica gel granular porous body having the bimodal hierarchical porous structure, was obtained. The supporting amount of palladium of the catalyst was measured from the weight percentage of Pd and Si in the catalyst measured using an energy dispersive X-ray fluorescence spectrometer (EDX-8000, manufactured by Shimadzu Corporation). Then, the supporting amount of palladium of the catalyst was calculated to be 1.62 wt % from the calculation formula of "(weight percentage of Pd)/(weight percentage of Si+weight percentage of O$_2$)×100."

Example 2

Atmospheric Method for Supporting Palladium in Acetonitrile 0.011 g of palladium acetate (5.2 mg, in terms of palladium) was dissolved in 10 mL of acetonitrile (preparation step B). Subsequently, 0.1 g of the granular porous body obtained in Production Example 1 was added, and the mixture was stirred at room temperature for 3.5 hours under an argon atmosphere. Thereafter, the resulting brown granular porous body was recovered by filtration, filtered and washed three times, each time with 10 mL of water and ethanol in order, and then dried in vacuum for 12 hours (impregnation step B). The filtrate generated in the impregnation step B was diluted with water to 100 mL, and the amount of palladium in the filtrate generated in the impregnation step B was measured with an atomic absorption spectrophotometer (AA-7000, manufactured by Shimadzu Corporation). The palladium concentration in the filtrate generated in the impregnation step B was 15.4 ppm, and 1.54 mg of palladium was present in 100 mL of the filtrate generated in the impregnation step B. From the difference between 5.2 mg of the added palladium amount and 1.54 mg of the palladium amount in the filtrate generated in the impregnation step B, it was confirmed that 3.6 mg of palladium was present in 0.1 g of the granular porous body after the impregnation step B treatment. Subsequently, the recovered brown granular porous body was stirred for two hours at room temperature under an argon atmosphere in 5 mL of an aqueous solution to which 7.2 μL of hydrazine was added (reduction step). Thereafter, the resulting brown granular porous body was recovered by filtration, filtered and washed three times, each time with 10 mL of water and methanol in order, and then dried under vacuum for 12 hours. The a catalyst in which palladium is supported by the silica gel granular porous body having a bimodal hierarchical porous structure was obtained (reducing agent removal step). The filtrate generated in the reducing agent removal step was condensed under reduced pressure and diluted with water to 100 mL, and the palladium amount in the filtrate generated in the reducing agent removing step was measured with an atomic absorption spectrophotometer. The palladium concentration in the filtrate generated in the reducing agent removal step was 0.88 ppm, and 0.088 mg of palladium was present in 100 mL of the filtrate generated in the reducing agent removal step. It was confirmed that the elution was less than 3% with respect to 3.6 mg of palladium present on the granular porous body after the impregnation step B treatment That is, palladium after the impregnation step B treatment was supported by 97% or more, and the supporting amount of palladium of the catalyst was calculated as 3.5 wt %.

Example 3

Atmospheric Method for Supporting Palladium in Methanol

A catalyst, in which palladium was supported on a silica gel granular porous body having a bimodal hierarchical porous structure, as obtained as in Example 2 by using the silica gel granular porous body having the bimodal hierarchical porous structure obtained in Production Example 1, except that methanol was used instead of acetonitrile, and the reduction step with hydrazine and the reducing agent removal step were not performed. That is, the impregnation step B, the reduction step and the reducing agent removal step wee successively performed in which methanol served as both the solvent and the reducing agent in the impregnation step B. When the supporting amount of palladium of the catalyst was calculated as in Example 2, the supporting amount of palladium was 3.5 wt %.

Example 4

Atmospheric Method for Supporting Palladium in Methanol

A catalyst, in which palladium was supported on a silica gel granular porous body having a bimodal hierarchical porous structure, was obtained as in Example 3 by using 0.5 g of the silica gel granular porous body having the bimodal hierarchical porous structure obtained in Production Example 2. When the supporting amount of palladium of the catalyst was calculated as in Example 2, the supporting amount of palladium was 3.5 wt %.

Example 5

Atmospheric Method for Supporting Palladium in Methanol

A catalyst in which palladium was supported on a silica gel granular porous body having a bimodal hierarchical porous structure, was obtained as in Example 3 by using 0.5 g of the silica gel granular porous body having the bimodal hierarchical porous structure obtained in Production Example 3. When the supporting amount of palladium of the catalyst was calculated as in Example 2, the supporting amount of palladium was 3.5 wt %.

Example 6

Supercritical Method for Supporting Palladium

A catalyst, in which palladium was supported on a silica gel granular porous body having a bimodal hierarchical porous structure, as obtained as in Example 1, except that 2 g of the silica gel granular porous body having the bimodal hierarchical porous structure obtained in Production Example 1 as used and palladium acetate and acetone were 0.1 g and 180 mL, respectively. When the supporting amount of palladium in the catalyst was measured as in Example 1, the supporting amount of palladium was 0.25 wt %.

Example 7

Supercritical Method for Supporting Palladium

A catalyst, in which palladium was supported on a silica gel granular porous body having a bimodal hierarchical porous structure, was obtained as in Example 1 by using the silica gel granular porous body having the bimodal hierarchical porous structure obtained in Production Example 2. When the supporting amount of palladium of the catalyst was measured as in Example 1, the supporting amount of palladium was 1.07 wt %.

Example 8

Supercritical Method for Supporting Palladium

A catalyst in which palladium was supported on a silica gel granular porous body having a bimodal hierarchical porous structure was obtained as in Example 1 by using the silica gel granular porous body having the bimodal hierarchical porous structure obtained in Production Example 3. When the supporting amount of palladium of the catalyst was measured as in Example 1, the supporting amount of palladium was 0.98 wt %.

Example 9

Supercritical Method for Supporting Palladium

A catalyst, in which palladium was supported on a silica gel granular porous body having a bimodal hierarchical porous structure, was obtained as in Example 1, except that 2.5 g of the silica gel granular porous body having the bimodal hierarchical porous structure obtained in Production Example 1 was used, the used amount of palladium acetate was 1 g, and the used amount of acetone was 180 mL. When the supporting amount of palladium in the catalyst was measured as in Example 1, the supporting amount of palladium was 0.25 wt %.

Example 10

Supercritical Method for Supporting Palladium

A catalyst, in which palladium was supported on a silica gel granular porous body having a bimodal hierarchical porous structure, was obtained as in Example 1, except that 2.5 g of the silica gel granular porous body having the bimodal hierarchical porous structure obtained in Production Example 1 was used, the used amount of palladium acetate was 0.1 g. and the used amount of acetone was 180 mL. When the supporting amount of palladium of the catalyst was measured as in Example 1, the supporting amount of palladium was 0.103 wt %.

Production Example of Titania Granular Porous Body Having Bimodal Hierarchical Porous Structure 0.7 g of polyethylene glycol (molecular weight 10,000) was dissolved in a solution in which 3.5 mL of ethyl acetoacetate and 2 mL of 1-propanol were mixed. Thereafter, 5 mL of isopropyl orthotitanate was added, and the minute was stirred. Then, 1 mL of 1 M ammonium nitrate aqueous solution was added dropwise, followed by stirring for one minute to obtain homogeneous solution. Then, a precursor sol was obtained. The resulting precursor sol was accommodated in a glass container. The container was closed and dipped in a hot water bath set at 40° C. to be heated for gelation. Then, a wet gel was obtained. The operation of immersing the resulting wet gel in 20 mL of 50% ethanol and washing at 40° C. overnight was repeated three times, and the gel was further immersed in 20 mL of water and washed at 80° C. overnight. Thereafter, the washed wet gel was air-dried, and the resulting dried gel was sintered at 500° C. for two hours to obtain a massive titania gel porous body having a bimodal hierarchical porous structure. The massive titania gel porous body was crushed lightly using a mortar to obtain a titania gel granular porous body having a bimodal hierarchical porous structure.

The resulting titania gel granular porous body having the bimodal hierarchical porous structure had the particle diameter of 20/63 μm, the through-hole diameter of 0.5 to 1.0 μm, and the average pore diameter of the pores of 10 nm. The particle diameter was determined using a JIS standard sieve, the through-hole diameter was determined from the void of the spherical particle skeleton in a scanning electron microscope (SEM) photographic image, and the average pore diameter of the pores was determined by a BJH method based on nitrogen adsorption measurement. Moreover, the pore diameter distribution and the specific surface area of the titania gel granular porous body having the bimodal hierarchical porous structure were measured by a nitrogen adsorption/desorption method, and the specific surface area was 110 $m^2/g$ as calculated by the BJH method.

Example 11

Supercritical Method for Supporting Palladium

A catalyst, in which palladium was supported on a silica gel granular porous body having a bimodal hierarchical porous structure, was obtained as in Example 1, except that a titania gel granular porous body having a bimodal hierarchical porous structure obtained in the above Production Example was used instead of 0.5 g of the silica gel granular porous body having the bimodal hierarchical porous structure obtained in the Production Example 1. When the supporting amount of palladium of the catalyst was measured as in Example 1, the supporting amount of palladium was 4.4 wt %.

Example 12

Atmospheric Method for Supporting Palladium in Acetone

A catalyst, in which palladium was supported on a silica gel granular porous body having a bimodal hierarchical porous structure, was obtained as in Example 2, except that acetone was used instead of acetonitrile. When the supporting amount of palladium of the catalyst was measured as in Example 1, the supporting amount of palladium was 1.6 wt %

Example 13

Atmospheric Method for Supporting Palladium in 2-propanol

A catalyst, in which palladium was supported on a silica gel granular porous body having a bimodal hierarchical porous structure, was obtained as in Example 12, except that 2-propanol was used instead of acetone. The supporting amount of palladium was 1.3 wt %.

Example 14

Atmospheric Method for Supporting Palladium in Tetrahydrofuran

A catalyst, in which palladium was supported on a silica gel granular porous body having a bimodal hierarchical porous structure, was obtained as in Example 12, except that tetrahydrofuran was used instead of acetone. When the supporting amount of palladium of the catalyst was measured as in Example 1, the supporting amount of palladium was 0.96 wt:

Comparative Example 1

Atmospheric Method for Supporting Palladium in Ethyl Acetate

A catalyst in which palladium was supported on a silica gel granular porous body having a bimodal hierarchical porous structure, was obtained as in Example 2, except that 10 mL of ethyl acetate was used instead of acetonitrile. When the supporting amount of palladium of the catalyst was calculated as in Example 2, the supporting amount of palladium was 3.5 wt %.

Comparative Example 2

Supercritical Method for Supporting Palladium on Conventional Silica Gel

A catalyst in which palladium was supported on a silica gel granular porous body, was obtained as in Example 1, except that 0.5 g of silica gel (particle diameter 20/63 μm, pore diameter 6 nm, specific surface area 550 $m^2/g$) not having a hierarchical porous structure manufactured by Merck was used instead of a silica gel granular porous body having a bimodal hierarchical porous structure. When the supporting amount of palladium of the catalyst was measured as in Example 1, the supporting amount of palladium was 0.3 wt %.

Test Example 1

The catalytic activity for each substrate was examined using the prepared catalysts. First, in order to examine the presence or absence of the selectivity of the reduction reaction for alkyne and alkene by using each catalyst, the catalytic activities were examined when diphenylacetylene was used as a reactant.

Test Example 1-1

Diphenylacetylene was dissolved in 1 mL of methanol so as to be 0.25 mol/L. Then the catalyst obtained in Example 6, in which palladium (Pd) is supported on the silica gel granular porous body having the bimodal hierarchical porous structure, was added so that the molar ratio of palladium of the catalyst to the reactant became 0.1 mol % The mixture was stirred at 25° C. for 22 hours under a hydrogen atmosphere. After the reduction reaction, the concentration ratio among the total of four components, which are diphenylacetylene, and cis-diphenylethylene, trans-diphenylethylene and 1,2-diphenylethane after the reduction, was analyzed by 1H-NMR, and the superiority and inferiority of the catalytic activity were compared based on the concentration ratio among cis-diphenylethylene, trans-diphenylethylene and 1,2-diphenylethane in the solution after the reaction.

Test Examples 1-2 and 1-3

For the respective palladium-supported catalysts obtained in Examples 2 and 3, the superiority and inferiority of the catalytic activities were compared as in Test Example 1-1, except that the respective stirring times were three hours and 24 hours.

Test Example 1-4

For the palladium-supported catalyst obtained in Example 11, the superiority and the inferiority of the catalytic activity were compared as in Test Example 1-1, except that the molar ratio of palladium of the catalyst to the reactant was 1 mol %, and the stirring time was 0.5 hours.

Test Example 1-5

For the palladium-supported catalyst obtained in Comparative Example 1, the superiority and inferiority of the catalytic activity was compared as in Test Example 1-1, except that the stirring time was 24 hours.

The results of comparing the catalytic activities are shown in the tables below. In Table 1-1, "used amount of catalyst [mol %]" means the molar ratio of palladium in the catalyst Specifically, it means the molar ratio of palladium of the catalyst to the reactant.

As shown in Tables 1-1 and 1-2, in the case of the supercritical method, diphenylacetylene was completely reduced to 1,2-diphenylethane in 22 hours (Test Example 1-1), and high catalytic activity was exhibited. Similar to the case of the supercritical method, also in the case of the atmospheric method using acetonitrile, diphenylacetylene was completely reduced to 1,2-diphenylethane, and the catalytic activity similar to that in the supercritical method was exhibited (Test Example 1-2). In the case of the atmospheric method using methanol, 23% of diphenylacetylene was unreacted, and moderate catalytic activity was exhibited (Test Example 1-3). By using titania as a carrier on which Pd was supported, diphenylacetylene was completely reduced to 1,2-diphenylethane in 0.5 hours (Test Example 1-4), and high catalytic activity was exhibited. In the case of the atmospheric method using ethyl acetate, 98% of diphenylacetylene was unreacted and no catalytic activity was exhibited (Test Example 1-5).

Test Example 2

In order to examine the presence or absence of the selectivity of the reduction reaction for an alkynyl group by using the catalysts prepared in Examples 2 to 4, the catalytic activities were examined when diphenylacetylene was used as a reactant.

TABLE 1-1

| Test Example | Pd Supported-Carrier | Pd Supporting method | Supercritical Fluid or Organic Solvent | Type of Silica Gel | Supporting Amount of Pd [wt %] | Used Amount of Catalyst [mol %] | Reaction (Stirring) Time [hour] |
|---|---|---|---|---|---|---|---|
| 1-1 | Example 6 | Supercritical Method | Carbon Dioxide | Bimodal Hierarchical Porous Structure | 0.25 | 0.025 | 22 |
| 1-2 | Example 2 | Atmospheric Method | Acetonitrile | Bimodal Hierarchical Porous Structure | 3.5 | 0.1 | 3 |
| 1-3 | Example 3 | Atmospheric Method | Methanol | Bimodal Hierarchical Porous Structure | 3.5 | 0.1 | 24 |
| 1-4 | Example 11 | Supercritical Method | Carbon Dioxide | Bimodal Hierarchical Porous Structure | 4.4 | 1 | 0.5 |
| 1-5 | Comparative Example 1 | Atmospheric Method | Ethyl Acetate | Bimodal Hierarchical Porous Structure | 3.5 | 0.1 | 24 |

TABLE 1-2

| Test Example | Diphenyl-acetylene | cis-diphenyl-ethylene | trans-diphenyl-ethylene | 1,2-diphenyl-ethane |
|---|---|---|---|---|
| 1-1 | 0 | 1 | 0 | 99 |
| 1-2 | 0 | 0 | 1 | 99 |
| 1-3 | 23 | 65 | 2 | 10 |
| 1-4 | 0 | 0 | 0 | 100 |
| 1-5 | 98 | 1 | 1 | 0 |

As shown in Tables 1-1 and 1-2, in Test Example 1-1, the concentration ratio among diphenylacetylene, cis-diphenylethylene, trans-diphenylethylene and 1,2-diphenylethane in the solution after the reaction was 0:1:0:99. In Test Example 1-2, the concentration ratio among diphenylacetylene, cis-diphenylethylene, trans-diphenylethylene and 1,2-diphenylethane in the solution after the reaction was 0:0:1:99. In Test Example 1-3, the concentration ratio among diphenylacetylene, cis-diphenylethylene, trans-diphenylethylene and 1,2-diphenylethane in the solution after reaction was 23:65:2:10. In Test Example 1-4, the concentration ratio among diphenylacetylene, cis-diphenylethylene, trans-diphenylethylene and 1,2-diphenylethane in the solution after the reaction was 0:0:0:100. In Test Example 1-5, the concentration ratio among diphenylacetylene, cis-diphenylethylene, trans-diphenylethylene and 1,2-diphenylethane in the solution after the reaction was 98:1:1:0.

Test Example 2-1

For the palladium-supported catalyst obtained in Example 4, the superiority and inferiority of the catalytic activity were compared as in Test Example 1-1, except that the stirring time was 66 hours.

Test Example 2-2

For the palladium-supported catalyst obtained in Example 5, the superiority and inferiority of the catalytic activity were compared as in Test Example 1-1, except that the stirring time was 66 hours.

The results of comparing the catalytic activities are shown in the tables below. In Table 2-1, "used amount of catalyst [mol %]" means the molar ratio of palladium in the catalyst. Specifically, it means the molar ratio of palladium of the catalyst to the reactant.

TABLE 2-1

| Test Example | Pd Supported-Carrier | Pd Supporting method | Organic Solvent | Type of Silica Gel | Supporting Amount of Pd [wt %] | Used Amount of Catalyst [mol %] | Reaction (Stirring) Time [hour] |
|---|---|---|---|---|---|---|---|
| 1-3 | Example 3 | Atmospheric Method | Methanol | Bimodal Hierarchical Porous Structure | 3.5 | 0.1 | 24 |
| 2-1 | Example 4 | Atmospheric Method | Methanol | Bimodal Hierarchical Porous Structure | 3.5 | 0.1 | 66 |
| 2-2 | Example 5 | Atmospheric Method | Methanol | Bimodal Hierarchical Porous Structure | 3.5 | 0.1 | 66 |

TABLE 2-2

| Test Example | Diphenyl-acetylene | cis-diphenyl-ethylene | trans-diphenyl-ethylene | 1,2-diphenyl-ethane |
|---|---|---|---|---|
| 1-3 | 23 | 65 | 2 | 10 |
| 2-1 | 0 | 15 | 1 | 81 |
| 2-2 | 0 | 55 | 3 | 42 |

As shown in Tables 2-1 and 2-2, in Test Example 2-1, the concentration ratio among diphenylacetylene, cis-diphenylethylene, trans-diphenylethylene and 1,2-diphenylethane in the solution after the reaction as 0:15:1:84. In Test Example 2-2, the concentration ratio among diphenylacetylene, cis-diphenylethylene, trans-diphenylethylene and 1,2-diphenylethane in the solution after the reaction was 0:55:3:42.

Since the reactant diphenylacetylene was reduced to cis-diphenylethylene and 1,2-diphenylethane as the main products in Test Examples 2-2 and 2-3, it was confirmed that the catalytic activities similar to that of the case (Test Example 1-3) of the catalyst created in Example 3 were exhibited.

Test Example 3

In order to examine the presence or absence of the selectivity of the reduction reaction for a nitro group by using each catalyst the catalytic activities were examined when p-ethylnitrobenzene was used as a reactant.

Test Example 3-1 p-ethylnitrobenzene was dissolved in 1 mL of methanol so as to be 0.25 mol/L. Then, the palladium-supported catalyst obtained in Example 1 was added so that the molar ratio of palladium of the catalyst to the reactant became 0.07 mol % The mixture was stirred at 25° C. for 21 hours under a hydrogen atmosphere. After the reduction reaction, the concentration ratio of p-ethylnitrobenzene to p-aminoethylbenzene after the reduction was analyzed by 1H-NMR.

Test Example 3-2

For the palladium-supported catalyst obtained in Example 2, the superiority and the inferiority of the catalytic activity were compared as in Test Example 3-1, except that the molar ratio of palladium of the catalyst to the reactant was 0.1 mol %, and the stirring time was 23 hours.

Test Example 3-3

For the palladium-supported catalyst obtained in Example 2, the superiority and the inferiority of the catalytic activity were compared as in Test Example 3-1, except that the molar ratio of palladium of the catalyst to the reactant was 0.1 mol %, and the stirring time was 17 hours.

Test Example 3-4

For the palladium-supported catalyst obtained in Example 6, the superiority and the inferiority of the catalytic activity were compared as in Test Example 3-1, except that the molar ratio of palladium of the catalyst to the reactant was 0.07 mol %, and the stirring time was two hours.

Test Example 3-5

For the palladium-supported catalyst obtained in Example 6, the superiority and the inferiority of the catalytic activity were compared as in Test Example 3-1, except that the molar ratio of palladium of the catalyst to the reactant was 0.025 mol %, and the stirring time was 2.5 hours.

Test Example 3-6

For the palladium-supported catalyst obtained in Example 7, the superiority and the inferiority of the catalytic activity were compared as in Test Example 3-1, except that the molar ratio of palladium of the catalyst to the reactant was 0.070 mol %, the stirring time was five hours, and 3 mL of methanol was used.

Test Example 3-7

For the palladium-supported catalyst obtained in Example 7, the superiority and the inferiority of the catalytic activity were compared as in Test Example 3-1, except that the molar ratio of palladium of the catalyst to the reactant was 0.016 mol %, the stirring time was five hours, and 3 mL of methanol was used.

Test Example 3-8

For the palladium-supported catalyst obtained in Example 8, the superiority and the inferiority of the catalytic activity were compared as in Test Example 3-1, except that the molar ratio of palladium of the catalyst to the reactant was 0.025 mol %, the stirring time was 18 hours, and 2 mL of methanol was used.

Test Example 3-9

For the palladium-supported catalyst obtained in Example 8, the superiority and the inferiority of the catalytic activity were compared as in Test Example 3-1, except that the molar ratio of palladium of the catalyst to the reactant was 0.025 mol %, the stirring time was six hours, and 2 mL of methanol was used.

Test Example 3-10

For the catalyst obtained in Example 11, in which palladium is supported on the titania gel granular porous body having the bimodal hierarchical porous structure, the superiority and the inferiority of the catalytic activity were compared as in Test Example 3-1, except that the molar ratio of palladium to the reactant was 1 mol %, and the stirring time was four hours.

The results of comparing the catalytic activities are shown in the tables below. In Table 3-1, "used amount of catalyst [mol %]" means the molar ratio of palladium in the catalyst. Specifically, it means the molar ratio of palladium of the catalyst to the reactant.

TABLE 3-1

| Test Example | Pd Supported-Carrier | Pd Supporting method | Supercritical Fluid or Organic Solvent | Type of Silica Gel | Supporting Amount of Pd [wt %] | Used Amount of Catalyst [mol %] | Reaction (Stirring) Time [hour] | Used Amout of Methanol [mL] |
|---|---|---|---|---|---|---|---|---|
| 3-1 | Example 1 | Supercritical Method | Carbon Dioxide | Bimodal Hierarchical Porous Structure | 1.62 | 0.07 | 21 | 1 |
| 3-2 | Example 2 | Atmospheric Method | Acetonitrile | Bimodal Hierarchical Porous Structure | 3.5 | 0.1 | 23 | 1 |
| 3-3 | Example 2 | Atmospheric Method | Acetonitrile | Bimodal Hierarchical Porous Structure | 3.5 | 0.1 | 17 | 1 |
| 3-4 | Example 6 | Supercritical Method | Carbon Dioxide | Bimodal Hierarchical Porous Structure | 0.25 | 0.07 | 2 | 1 |
| 3-5 | Example 6 | Supercritical Method | Carbon Dioxide | Bimodal Hierarchical Porous Structure | 0.25 | 0.025 | 2.5 | 1 |
| 3-6 | Example 7 | Supercritical Method | Carbon Dioxide | Bimodal Hierarchical Porous Structure | 1.07 | 0.07 | 5 | 3 |
| 3-7 | Example 7 | Supercritical Method | Carbon Dioxide | Bimodal Hierarchical Porous Structure | 1.07 | 0.016 | 5 | 3 |
| 3-8 | Example 8 | Supercritical Method | Carbon Dioxide | Bimodal Hierarchical Porous Structure | 0.98 | 0.025 | 18 | 2 |
| 3-9 | Example 8 | Supercritical Method | Carbon Dioxide | Bimodal Hierarchical Porous Structure | 0.98 | 0.025 | 6 | 2 |
| 3-10 | Example 11 | Supercritical Method | Carbon Dioxide | Bimodal Hierarchical Porous Structure | 4.4 | 1 | 4 | 1 |

TABLE 3-2

| Test Example | p-ethylnitrobenzene | p-aminoethylbenzene |
|---|---|---|
| 3-1 | 0 | 100 |
| 3-2 | 0 | 100 |
| 3-3 | 0 | 100 |
| 3-4 | 0 | 100 |
| 3-5 | 1 | 99 |
| 3-6 | 0 | 100 |
| 3-7 | 0 | 100 |
| 3-8 | 0 | 100 |
| 3-9 | 0 | 100 |
| 3-10 | 0 | 100 |

As shown in Table 3-2, in Test Examples 3-1 to 3-4 and 3-6 to 3-10, the concentration ratio of p-ethylnitrobenzene to p-aminoethylbenzene after the reduction in the solution after the reduction reaction was 0:100, indicating that the reduction reaction had completely progressed. In Test Example 3-5, the concentration ratio of p-ethylnitrobenzene to p-aminoethylbenzene after the reduction in the solution after the reduction reaction was 1:99, indicating that the reduction reaction had progressed almost completely. These results showed that both palladium supporting by the supercritical method and palladium supporting by the atmospheric method in acetonitrile are supporting methods resulting in suitable catalytic activities exhibition.

Test Example 4

In order to examine the presence or absence of the selectivity of the reduction reaction for a nitro group by using the catalyst prepared in Example 2, the catalytic activity was examined when 2'-nitroacetanilide was used as a reactant.

2'-nitroacetanilide was dissolved in 1 mL of methanol to be 0.25 mol/L. Then, the catalyst obtained in Example 2, in which palladium is supported on the silica gel granular porous body having the bimodal hierarchical porous structure, was added so that the molar ratio of palladium to the reactant became 0.1 mol % The mixture was stirred at 25° C. for 24 hours under a hydrogen atmosphere. The concentration ratio between the total of two components, which are 2'-nitroacetanilide after the reduction reaction and 2'-aminoacetanilide after the reduction, was analyzed by $^{1}$H-NMR, and the catalytic activities were compared based on the concentration of 2'-nitroacetanilide in the solution after the reduction reaction. Since 100% of 2'-nitroacetanilide was reduced to 2'-aminoacetanilide in 24 hours, the palladium-supported catalyst obtained in Example 2 exhibited suitable catalytic activity.

Test Example 5

The catalytic activities of the silica gel granular porous body obtained in Example 1, which has the bimodal hierarchical porous structure supporting palladium, and the silica gel granular porous body obtained in Comparative Example 2, which does not have the hierarchical porous structure supporting palladium, were investigated by the reduction reaction of styrene to ethylbenzene 0.5 g of styrene, a reactant, was dissolved in 25 mL of methanol and placed in an Erlenmeyer flask. Then, the silica gel granular porous body obtained in Example 1, which has the bimodal hierarchical porous structure supporting palladium, was added so that the molar ratio of palladium of the catalyst to the reactant became 0.1 mol %. The mixture was stirred at 20° C. for two hours under a hydrogen atmosphere. The concentration ratio of styrene present in the solution after the reduction reaction to ethylbenzene after the reduction was analyzed by $^{1}$H-NMR, and the superiority and the inferiority of the catalytic activity were compared based on the concentration of ethylbenzene relative to the concentration of styrene in the solution after the reduction reaction.

Similarly, the superiority and the inferiority of the catalytic activity were compared also for the silica gel granular porous body obtained in Comparative Example 2, which does not have a hierarchical porous structure supporting palladium.

Figure 4:
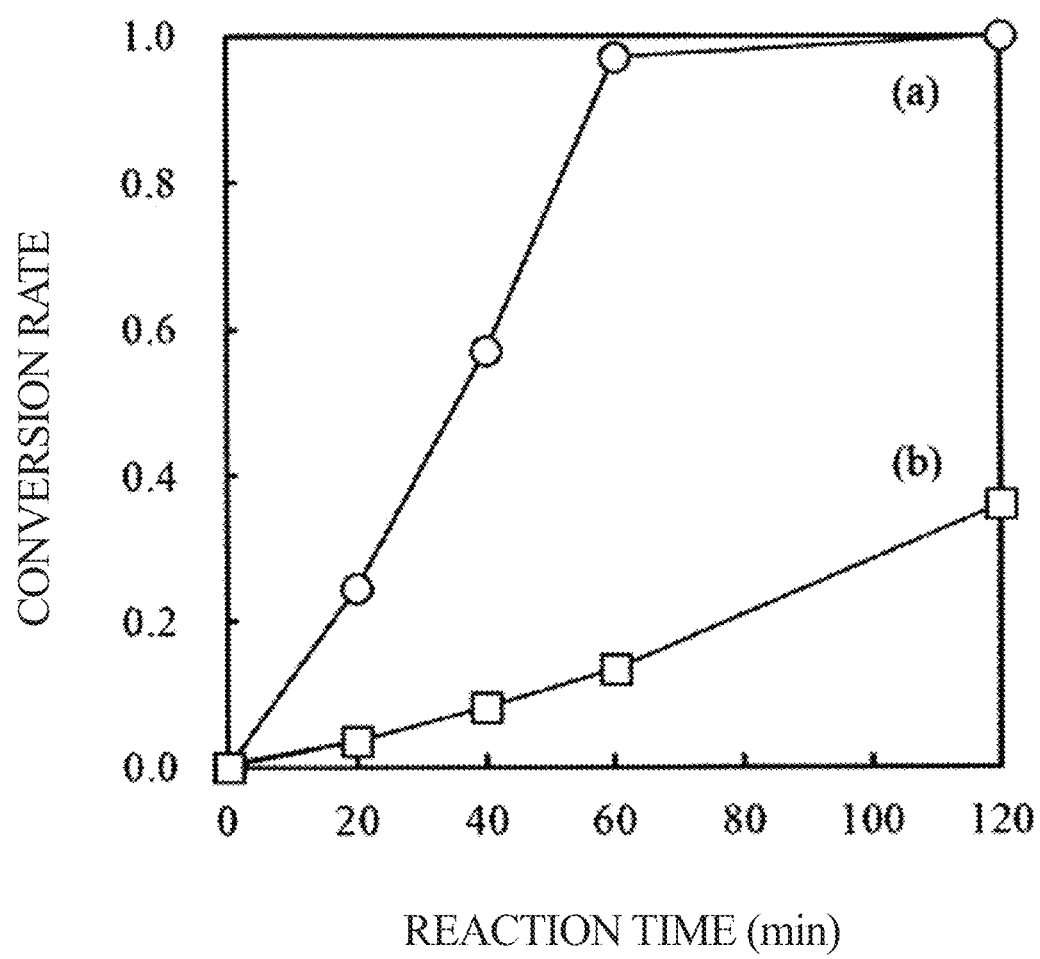
FIG. 4 is a diagram showing the respective measurement results of reduction reaction of styrene to ethylbenzene in methanol by using as catalysts the silica gel granular porous body (a) obtained in Example 1, which has the bimodal hierarchical porous structure supporting palladium, and the silica gel granular porous body (b) obtained in Comparative Example 2, which does not have a hierarchical porous structure supporting palladium. The horizontal axis indicates the reaction time (minute), and the vertical axis indicates the conversion rate (reduction rate) from styrene to ethylbenzene. As the value approaches 1.0 on the vertical axis, the concentration of ethylbenzene becomes higher than the concentration of styrene, indicating that the reduction reaction is progressing.

FIG. 4 shows the results of comparing the catalytic activities. In FIG. 4, the horizontal axis indicates the stirring time (reaction time) (minute), and the vertical axis indicates the conversion rate (reduction rate) from styrene to ethylbenzene. As the value approaches 1.0 on the vertical axis, the concentration of ethylbenzene becomes higher than the concentration of styrene, indicating that the reduction reaction is progressing. Since the reduction reaction of styrene to ethylbenzene had progressed more in the silica gel granular porous body (a) obtained in Example 1, which has the bimodal hierarchical porous structure supporting palladium, than in the silica gel granular porous body (b) obtained in Comparative Example 2, which does not have a hierarchical porous structure supporting palladium, the catalytic activity of the silica gel granular porous body (a) was exhibited to be better.

Test Example 6

In order to examine the presence or absence of the selectivity of the reduction reaction for an azido group by using the catalyst prepared in Example 6, the catalytic activity was examined when 1-azido-4-ethylbenzene was used as a reactant.

1-azido-4-ethylbenzene was dissolved in 1 mL of methanol so as to be 0.25 mol/L. Then, the palladium-supported catalyst obtained in Example 6 was added so that the molar ratio of palladium of the catalyst to the reactant became 0.025 mol %. The mixture was stirred at 25° C. for three hours under a hydrogen atmosphere. After the reduction reaction, the concentration ratio of unreacted 1-azido-4-ethylbenzene to p-ethylaniline after the reduction was analyzed by 1H-NMR.

The results of comparing the catalytic activities are shown in the tables below. In Table 4-1, "used amount of catalyst [mol %]" means the molar ratio of palladium in the catalyst. Specifically, it means the molar ratio of palladium of the catalyst to the reactant.

TABLE 4-1

| Test Example | Pd Supported-Carrier | Pd Supporting method | Supercritical Fluid | Type of Silica Gel | Supporting Amount of Pd [wt %] | Used Amount of Catalyst [mol %] | Reaction (Stirring) Time [hour] |
|---|---|---|---|---|---|---|---|
| 6 | Example 6 | Supercritical Method | Carbon Dioxide | Bimodal Hierarchical Porous Structure | 0.25 | 0.025 | 3 |

TABLE 4-2

| Test Example | 1-azido-4-etnylbenzene | p-ethylaniline |
|---|---|---|
| 6 | 0 | 100 |

As shown in Table 4-2, in Test Example 6, after the reduction reaction, the concentration ratio of unreacted 1-azido-ethylbenzene and 4-ethylaniline after the reduction was 0:100.

Test Example 7

In order to examine the presence or absence of the selectivity of the reduction reaction for an azido group by using the catalyst prepared in Example 2, the catalytic activity was examined when 4-azidobenzoic acid was used as a reactant.

4-azidobenzoic acid was dissolved in 1 mL of methanol so as to be 0.25 moL/L. Then, the palladium-supported catalyst obtained in Example 2 was added so that the molar ratio of palladium of the catalyst to the reactant became 0.1 mol % The mixture as stirred at 25° C. for 24 hours under a hydrogen atmosphere. After the reduction reaction, the concentration ratio of unreacted 4-azidobenzoic acid to 4-aminobenzoic acid after the reduction was analyzed by 1H-NMR The results of comparing the catalytic activities are shown in the tables below. In Table 5-1, "used amount of catalyst [mol %]" means the molar ratio of palladium in the catalyst. Specifically, it means the molar ratio of palladium of the catalyst to the reactant.

TABLE 5-1

| Test Example | Pd Supported-Carrier | Pd Supporting Method | Organic Solvent | Type of Silica Gel | Supporting Amount of Pd [wt %] | Used Amount of Catalyst [mol %] | Reaction (Stirring) Time [hour] |
|---|---|---|---|---|---|---|---|
| 7 | Example 2 | Atmospheric Method | Acetonitrile | Bimodal Hierarchical Porous Structure | 3.5 | 0.1 | 24 |

TABLE 5-2

| Test Example | 4-azidobenzoic acid | 4-aminobenzoic acid |
|---|---|---|
| 7 | 60 | 40 |

As shown in Table 5-2, in Test Example 7, after the reduction reaction, the concentration ratio of 4-azidobenzoic acid to 4-aminobenzoic acid after the reduction was 60:40, indicating that the catalytic activity was moderate.

Test Example 8

In order to examine the presence or absence of the selectivity of the reduction reaction for an aromatic N-Cbz group by using the catalysts prepared in Examples 2 and 6, the catalytic activities were examined when benzyl N-allyl-N-phenylcarbamate was used as a reactant.

Test Example 8-1

Benzyl N-allyl-N-phenylcarbamate was dissolved in 1 mL of methanol so as to be 0.25 mol/L. Then, the palladium-supported catalyst obtained in Example 2 was added so that the molar ratio of palladium of the catalyst to the reactant became 0.1 mol %. The mixture was stirred at 25° C. for 24 hours under a hydrogen atmosphere. After the reduction reaction, the concentration ratio among unreacted benzyl N-allyl-N-phenylcarbamate, and benzyl N-propyl-N-phenylcarbamate and N-propylaniline after the reduction was analyzed by 1H-NMR.

Test Example 8-2

For the palladium-supported catalyst obtained in Example 6, the superiority and the inferiority of the catalytic activity were compared as in Test Example 8-1, except that the molar ratio of palladium of the catalyst to the reactant was 0.025 mol %.

Test Example 8-3

For the palladium-supported catalyst obtained in Example 6, the superiority and the inferiority of the catalytic activity were compared similarly, except that the molar ratio of palladium of the catalyst to the reactant was 0.070 mol %, and the stirring time was five hours.

The results of comparing the catalytic activities are shown in the tables below. In Table 6-1, "used amount of catalyst [mol %]" means the molar ratio of palladium in the catalyst. Specifically, it means the molar ratio of palladium of the catalyst to the reactant.

TABLE 6-2

| Test Example | Benzyl N-allyl-N-phenylcarbamate | Benzyl N-propyl-N-phenylcarbamate | N-propylaniline |
|---|---|---|---|
| 8-1 | 0 | 82 | 18 |
| 8-2 | 0 | 71 | 29 |
| 8-3 | 0 | 0 | 100 |

As shown in Table 6-2, in Test Example 8-1, after the reduction reaction, the concentration ratio among unreacted benzyl N-allyl-N-phenylcarbamate, and benzyl N-propyl-N-phenylcarbamate and N-propylaniline after the reduction was 0:82:18. In Test Example 8-2, after the reduction reaction, the concentration ratio among unreacted benzyl N-allyl-N-phenylcarbamate, and benzyl N-propyl-N-phenylcarbamate and N-propylaniline after the reduction was 0:71:29. In Test Example 8-3, after the reduction reaction, the concentration ratio among unreacted benzyl N-allyl-N-phenylcarbamate, and benzyl N-propyl-N-phenylcarbamate and N-propylaniline after the reduction was 0:0:100. The results of Test Examples 8-2 and 8-3 showed that the catalytic activity was excellent when the molar ratio of palladium of the catalyst was increased although reaction time was short.

Test Example 9

In order to examine the presence or absence of the selectivity of the reduction reaction for an aliphatic N-Cbz group by using the catalysts prepared in Examples 2, 6 and 11, the catalytic activities were examined when benzyl N-(2-phenethyl)carbamate was used as a reactant.

Test Example 9-1

Benzyl N-(2-phenethyl)carbamate was dissolved in 1 mL of methanol so as to be 0.25 mol/L. Than, the palladium supported catalyst obtained in Example 2 was added so that the molar ratio of palladium of the catalyst to the reactant became 0.1 mol %. The mixture was stirred at 25° C. for two hours under a hydrogen atmosphere. After the reduction reaction, the concentration ratio of unreacted benzyl N-(2-phenethyl)carbamate to phenethylamine after the reduction was analyzed by 1H-NMR Test Example 9-2

For the palladium-supported catalyst obtained in Example 2, the superiority and the inferiority of the catalytic activity were compared as in Test Example 9-1, except that the molar ratio of palladium of the catalyst to the reactant was 1.0 mol %, and the stirring time was 24 hours.

TABLE 6-1

| Test Example | Pd Supported-Carrier | Pd Supporting Method | Supercritical Fluid or Organic Solvent | Type of Silica Gel | Supporting Amount of Pd [wt %] | Used Amount of Catalyst [mol %] | Reaction (Stirring) Time [hour] |
|---|---|---|---|---|---|---|---|
| 8-1 | Example 2 | Atmospheric Method | Acetonitrile | Bimodal Hierarchical Porous Structure | 3.5 | 0.1 | 24 |
| 8-2 | Example 6 | Supercritical Method | Carbon Dioxide | Bimodal Hierarchical Porous Structure | 0.25 | 0.025 | 24 |
| 8-3 | Example 6 | Supercritical Method | Carbon Dioxide | Bimodal Hierarchical Porous Structure | 0.25 | 0.07 | 5 |

Test Example 9-3

For the palladium-supported catalyst obtained in Example 6, the superiority and the inferiority of the catalytic activity were compared as in Test Example 9-1, except that the molar ratio of palladium of the catalyst to the reactant we 0.025 mol %, and the stirring time was seven hours.

Test Example 9-4

For the palladium-supported catalyst obtained in Example 11, the superiority and the inferiority of the catalytic activity were compared as in Test Example 9-1, except that the molar ratio of palladium of the catalyst to the reactant was 1 mol %, and the stirring time was two hours.

The results of comparing the catalytic activities are shown in the tables below. In Table 7-1, "used amount of catalyst [mol %]" means the molar ratio of palladium in the catalyst. Specifically, it means the molar ratio of palladium of the catalyst to the reactant.

TABLE 7-1

| Test Example | Pd Supported-Carrier | Pd Supporting Method | Supercritical Fluid or Organic Solvent | Type of Silica Gel | Supporting Amount of Pd [wt %] | Used Amount of Catalyst [mol %] | Reaction (Stirring) Time [hour] |
|---|---|---|---|---|---|---|---|
| 9-1 | Example 2 | Atmospheric Method | Acetonitrile | Bimodal Hierarchical Porous Structure | 3.5 | 0.1 | 2 |
| 9-2 | Example 2 | Atmospheric Method | Acetonitrile | Bimodal Hierarchical Porous Structure | 3.5 | 1 | 24 |
| 9-3 | Example 6 | Supercritical Method | Carbon Dioxide | Bimodal Hierarchical Porous Structure | 0.25 | 0.025 | 7 |
| 9-4 | Example 11 | Supercritical Method | Carbon Dioxide | Bimodal Hierarchical Porous Structure | 4.4 | 1 | 72 |

TABLE 7-2

| Test Example | Benzyl N-(2-phenethyl)carbamate | Phenethylamine |
|---|---|---|
| 9-1 | 100 | 0 |
| 9-2 | 100 | 0 |
| 9-3 | 0 | 100 |
| 9-4 | 0 | 100 |

As shown in Table 7-2, in Test Examples 9-1 and 9-2, after the reduction reaction, the concentration ratio of unreacted benzyl N-(2-phenethyl)carbamate to phenethylamine after the reduction was 100:0. In Test Examples 9-3 and 9-4, after reduction reaction, the concentration ratio of unreacted benzyl N-(2-phenethyl)carbamate to phenethylamine after the reduction was 0:100. From the results of Test Examples 9-1 and 9-2, when the Pd-supported carrier of Example 2 was used, benzyl N-(2-phenethyl)carbamate was not reduced, and the catalytic activity was not exhibited for the aliphatic N-Cbz group. However, from the results of Test Examples 9-3 and 9-4, when the Pd-supported carriers of Examples 6 and 11 were used, benzyl N-(2-phenethyl) carbamate was reduced, and it was confirmed that the catalytic activities were exhibited for the aliphatic N-Cbz group.

Test Example 10

In order to examine the presence or absence of the selectivity of the reduction reaction for an aromatic ketone group by using the catalysts prepared in Examples 2 and 6, the catalytic activities were examined when phenyl isopropyl ketone was used as a reactant.

Test Example 10-1

Phenyl isopropyl ketone was dissolved in 1 mL of methanol so as to be 0.25 mol/L. Then, the palladium-supported catalyst obtained in Example 2 was added so that the molar ratio of palladium of the catalyst to the reactant became 0.1 mol %. The mixture was stirred at 25° C. for 24 hours under a hydrogen atmosphere. After the reduction reaction, the concentration ratio of unreacted phenyl isopropyl ketone to 2-methyl-1-phenylpropanol was analyzed by 1H-NMR.

Test Example 10-2

For the palladium-supported catalyst obtained in Example 6, the superiority and the inferiority of the catalytic activity were compared as in Test Example 10-1, except that the molar ratio of palladium of the catalyst to the reactant was 0.025 mol %, and the stirring was at 50° C. for 24 hours under a hydrogen atmosphere.

The results of comparing the catalytic activities are shown in the tables below. In Table 8-1, "used amount of catalyst [mol %]" means the molar ratio of palladium in the catalyst. Specifically, it means the molar ratio of palladium of the catalyst to the reactant.

TABLE 8-1

| Test Example | Pd Supported-Carrier | Pd Supporting Method | Supercritical Fluid or Organic Solvent | Type of Silica Gel | Supporting Amount of Pd [wt %] | Used Amount of Catalyst [mol %] | Reaction (Stirring) Time [hour] | Reaction (Stirring) Temperature [° C.] |
|---|---|---|---|---|---|---|---|---|
| 10-1 | Example 2 | Atmospheric Method | Acetonitrile | Bimodal Hierarchical Porous Structure | 3.5 | 0.1 | 24 | 25 |
| 10-2 | Example 6 | Supercritical Method | Carbon Dioxide | Bimodal Hierarchical Porous Structure | 0.25 | 0.025 | 24 | 50 |

TABLE 8-2

| Test Example | Phenyl isopropyl ketone | 2-methyl-1-phenylpropanol |
|---|---|---|
| 10-1 | 100 | 0 |
| 10-2 | 1 | 99 |

TABLE 9-2

| Test Example | Benzophenone | Benzhydrol | Diphenylmethane |
|---|---|---|---|
| 11 | 0 | 83 | 17 |

As shown in Table 8-2, in Test Example 10-1, after the reduction reaction, the concentration ratio of unreacted phenyl isopropyl ketone to 2-methyl-1-phenylpropanol after the reduction was 100:0. In Test Example 10-2, after the reduction reaction, the concentration ratio of unreacted phenyl isopropyl ketone to 2-methyl-1-phenylpropanol after the reduction was 1:99. From the results of Test Example 10-1, it was confirmed that the catalyst of the present invention supporting palladium at normal pressure did not exhibit catalytic activity for the aromatic ketone group when the Pd-supported carrier of Example 2 was used. From the results of Test Example 10-2, it was confirmed that the catalyst of the present invention supporting palladium by the supercritical method exhibited catalytic activity for the aromatic ketone group.

Test Example 11

In order to examine the presence or absence of the selectivity of the reduction reaction for an aromatic ketone group by using the catalyst prepared in Example 11, the catalytic activity was examined when benzophenone ketone was used as a reactant.

Benzophenone was dissolved in 1 mL of methanol so as to be 0.25 mol/L. Then, the palladium-supported catalyst obtained in Example 11 was added so that the molar ratio of palladium of the catalyst to the reactant became 1 mol % The mixture was stirred at 25° C. for 24 hours under a hydrogen atmosphere. After the reduction reaction, the concentration ratio among unreacted benzophenone, and benzhydrol and diphenylmethane after the reduction was analyzed by 1H-NMR The results of comparing the catalytic activities are shown in the tables below. In Table 9-1, "used amount of catalyst [mol %]" means the molar ratio of palladium in the catalyst. Specifically, it means the molar ratio of palladium of the catalyst to the reactant.

As shown in Table 9-2, in Test Example 11, after the reduction reaction, the concentration ratio among unreacted benzophenone, and benzhydrol and diphenylmethane after the reduction was 0:83:17. From the results of Test Example 11, it was confirmed that the catalyst of the present invention supporting palladium by the supercritical method exhibited catalytic activity for the aromatic ketone group.

Test Example 12

In order to examine the presence or absence of the selectivity of the reduction reaction for a benzyl ester group by using the catalysts prepared in Examples 2, 6 and 11, the catalytic activities were examined when benzyl cinnamate was used as a reactant.

Test Example 12-1

Benzyl cinnamate was dissolved in 1 mL of methanol so as to be 0.25 mol/L Then, the palladium-supported catalyst obtained in Example 2 was added so that the molar ratio of palladium of the catalyst to the reactant became 0.1 mol %. The mixture was stirred at 25° C. for 24 hours under a hydrogen atmosphere. After the reduction reaction, the concentration ratio among unreacted benzyl cinnamate, and benzyl 3-phenylpropionate and 3-phenylpropionic acid after the reduction was analyzed by 1H-NMR.

Test Example 12-2

For the palladium-supported catalyst obtained in Example 6, the superiority, and the inferiority of the catalytic activity were compared as in Test Example 12-1, except that the molar ratio of palladium of the catalyst to the reactant was 0.025 mol %.

TABLE 9-1

| Test Example | Pd Supported-Carrier | Pd Supporting Method | Supercritical Fluid | Type of Silica Gel | Supporting Amount of Pd [wt %] | Used Amount of Catalyst [mol %] | Reaction (Stirring) Time [hour] |
|---|---|---|---|---|---|---|---|
| 11 | Example 11 | Supercritical Method | Carbon Dioxide | Bimodal Hierarchical Porous Structure | 4.4 | 1 | 24 |

Test Example 12-3

For the palladium-supported catalyst obtained in Example 11, the superiority and the inferiority of the catalytic activity were compared as in Test Example 12-1, except that the molar ratio of palladium of the catalyst to the reactant was 1 mol %.

The results of comparing the catalytic activities are shown in the tables below. In Table 10-1, "used amount of catalyst [mol %]" means the molar ratio of palladium in the catalyst. Specifically, it means the molar ratio of palladium of the catalyst to the reactant.

TABLE 10-1

| Test Example | Pd Supported-Carrier | Pd Supporting Method | Supercritical Fluid or Organic Solvent | Type of Silica Gel | Supporting Amount of Pd [wt %] | Used Amount of Catalyst [mol %] | Reaction (Stirring) Time [hour] |
|---|---|---|---|---|---|---|---|
| 12-1 | Example 2 | Atmospheric Method | Acetonitrile | Bimodal Hierarchical Porous Structure | 3.5 | 0.1 | 24 |
| 12-2 | Example 6 | Supercritical Method | Carbon Dioxide | Bimodal Hierarchical Porous Structure | 0.25 | 0.025 | 24 |
| 12-3 | Example 11 | Supercritical Method | Carbon Dioxide | Bimodal Hierarchical Porous Structure | 4.4 | 1 | 24 |

TABLE 10-2

| Test Example | Benzyl cinnamate | Benzyl 3-phenylpropionate | 3-phenylpropionic acid |
|---|---|---|---|
| 12-1 | 0 | 100 | 0 |
| 12-2 | 0 | 78 | 22 |
| 12-3 | 0 | 0 | 100 |

As shown in Table 10-2, in Test Example 12-1, after the reduction reaction, the concentration ratio among unreacted benzyl cinnamate, and benzyl 3-phenylpropionate and 3-phenylpropionic acid after the reduction was 0:100:0. In Test Example 12-2, after the reduction reaction, the concentration ratio among unreacted benzyl cinnamate, and benzyl 3-phenylpropionate and 3-phenylpropionic acid after the reduction was 0:78:22. In Test Example 12-3, after the reduction reaction, the concentration ratio among unreacted benzyl cinnamate, and benzyl 3-phenylpropionate and 3-phenylpropionic acid after the reduction was 0:0:100. From these results, it was confirmed that the catalysts of the present invention supporting palladium by the atmospheric method did not exhibit catalytic activity for the benzyl ester group, whereas the catalysts of the present invention supporting palladium by the supercritical method exhibited catalytic activities for the benzyl ester group.

Test Example 13

In order to examine the presence or absence of the selectivity of the reduction reaction for a benzyl ester group by using the catalysts prepared in Examples 2 and 6, the catalytic activities were examined when benzyl benzoate was used as a reactant.

Test Example 13-1

Benzyl benzoate was dissolved in 1 mL of methanol so as to be 0.25 mol/L. Then, the palladium-supported catalyst obtained in Example 2 was added so that the molar ratio of palladium of the catalyst to the reactant became 0.1 mol %. The mixture was stirred at 25° C. for 24 hours under a hydrogen atmosphere. After the reduction reaction, the concentration ratio of unreacted benzyl benzoate to benzoic acid after the reduction was analyzed by 1H-NMR

Test Example 13-2

For the palladium-supported catalyst obtained in Example 6, the superiority and the inferiority of the catalytic activity were compared as in Test Example 13-1, except that the molar ratio of palladium of the catalyst to the reactant was 0.025 mol %, and the stirring time was six hours.

The results of comparing the catalytic activities are shown in the tables below. In Table 11-1, "used amount of catalyst [mol %]" means the molar ratio of palladium in the catalyst. Specifically, it means the molar ratio of palladium of the catalyst to the reactant.

TABLE 11-1

| Test Example | Pd Supported-Carrier | Pd Supporting Method | Supercritical Fluid or Organic Solvent | Type of Silica Gel | Supporting Amount of Pd [wt %] | Used Amount of Catalyst [mol %] | Reaction (Stirring) Time [hour] |
|---|---|---|---|---|---|---|---|
| 13-1 | Example 2 | Atmospheric Method | Acetonitrile | Bimodal Hierarchical Porous Structure | 3.5 | 0.1 | 24 |
| 13-2 | Example 6 | Supercritical Method | Carbon Dioxide | Bimodal Hierarchical Porous Structure | 0.25 | 0.025 | 6 |

TABLE 11-2

| Test Example | Benzyl Benzoate | Benzoic Acid |
|---|---|---|
| 13-1 | 100 | 0 |
| 13-2 | 69 | 31 |

As shown in Table 11-2, in Test Example 13-1, after the reduction reaction, the concentration ratio of unreacted benzyl benzoate to benzoic acid after the reduction was 100:0. In Test Example 13-2, after the reduction reaction, the concentration ratio of unreacted benzyl benzoate to benzoic acid after the reduction was 69:31. From these results, it was confirmed that the catalyst of the present invention supporting palladium by the supercritical method exhibited catalytic activity for the benzyl ester group.

Test Example 14

In order to examine the presence or absence of the selectivity of the reduction reaction for a halogen atom on an aromatic ring by using the catalysts prepared in Examples 6 and 11, the catalytic activities were examined when 4-chlorodiphenylmethane was used as a reactant.

Test Example 14-1

4-chlorodiphenylmethane was dissolved in 1 mL of methanol so as to be 0.25 mol/L. Then the palladium-supported catalyst obtained in Example 6 was added so that the molar ratio of palladium of the catalyst to the reactant became 0.025 mol %. The mixture was stirred at 25° C. for 20 hours under a hydrogen atmosphere. After the reduction reaction, the concentration ratio of unreacted 4-chlorodiphenylmethane to diphenylmethane after the reduction was analyzed by 1H-NMR.

Test Example 14-2

For the palladium supported catalyst obtained in Example 11, the superiority and the inferiority of the catalytic activity were compared as in Test Example 14-1, except that the molar ratio of palladium of the catalyst to the reactant was 1 mol %, and the reaction time is 24 hours.

Test Example 14-3

4-chlorodiphenylmethane was dissolved in 1 mL of methanol so as to be 0.25 mol/L Then, the palladium-supported catalyst obtained in Example 11 was added so that the molar ratio of palladium of the catalyst to the reactant became 1 mol %. Moreover, triethylamine was added so as to be one mole equivalent to the reactant, and the mixture was stirred at 25° C. for 24 hours under a hydrogen atmosphere. After the reduction reaction, the concentration ratio of unreacted 4-chlorodiphenylmethane to diphenylmethane after the reduction was analyzed by 1H-NMR The results of comparing the catalytic activities are shown in the tables below. In Table 12-1, "used amount of catalyst [mol %]" means the molar ratio of palladium in the catalyst. Specifically, it means the molar ratio of palladium of the catalyst to the reactant.

TABLE 12-2

| Test Example | 4-chlorodiphenylmethane | Diphenylmethane |
|---|---|---|
| 14-1 | 0 | 100 |
| 14-2 | 8 | 92 |
| 14-3 | 0 | 100 |

As shown in Table 12-2, in Test Example 14-1, after the reduction reaction, the concentration ratio of unreacted 4-chlorodiphenylmethane to diphenylmethane after the reduction was 100:0. In Test Example 14-2, after the reduction reaction, the concentration ratio of unreacted 4-chlorodiphenylmethane to diphenylmethane after the reduction was 8:92. In Test Example 14-3, after the reduction reaction, the concentration ratio of unreacted 4-chlorodiphenylmethane to diphenylmethane after the reduction was 0:100. From the results of Test Examples 14-2 and 14-3, it was confirmed that the catalysts of the present invention supporting palladium by the supercritical method exhibited the catalytic activities for the halogen atom on the aromatic ring by adding triethylamine so as to be one equivalent to the reactant.

Test Example 15

In order to examine the presence or absence of the selectivity of the reduction reaction for an aromatic benzyl ether group by using the catalyst prepared in Examples 6, the catalytic activity was examined when benzyl phenyl ether was used as a reactant.

Benzyl phenyl ether was dissolved in 1 mL of methanol so as to be 0.25 mol/L. Then, the palladium-supported catalyst obtained in Example 6 was added so that the molar ratio of palladium to the reactant became 0.1 mol %. The mixture was stirred at 25° C. for 24 hours under a hydrogen atmosphere. After the reduction reaction, the concentration ratio of unreacted benzyl phenyl ether to phenol after the reduction was analyzed by 1H-NMR The results of comparing the catalytic activities are shown in the tables below. In Table 13-1. "used amount of catalyst [mol %]" means the molar ratio of palladium in the catalyst Specifically; it means the molar ratio of palladium of the catalyst to the reactant.

TABLE 12-1

| Test Example | Pd Supported-Carrier | Pd Supporting Method | Supercritical Fluid | Type of Silica Gel | Supporting Amount of Pd [wt %] | Used Amount of Catalyst [mol %] | Reaction (Stirring) Time [hour] | Added Amount of Triethylamine to Reactant [equivalent] |
|---|---|---|---|---|---|---|---|---|
| 14-1 | Example 6 | Supercritical Method | Carbon Dioxide | Bimodal Hierarchical Porous Structure | 0.25 | 0.025 | 20 | — |
| 14-2 | Example 11 | Supercritical Method | Carbon Dioxide | Bimodal Hierarchical Porous Structure | 4.4 | 1 | 24 | — |
| 14-3 | Example 11 | Supercritical Method | Carbon Dioxide | Bimodal Hierarchical Porous Structure | 4.4 | 1 | 24 | 1 |

TABLE 13-1

| Test Example | Pd Supported-Carrier | Pd Supporting Method | Supercritical Fluid | Type of Silica Gel | Supporting Amount of Pd [wt %] | Used Amount of Catalyst [mol %] | Reaction (Stirring) Time [hour] |
|---|---|---|---|---|---|---|---|
| 15 | Example 6 | Supercritical Method | Carbon Dioxide | Bimodal Hierarchical Porous Structure | 0.25 | 0.1 | 24 |

TABLE 13-2

| Test Example | Benzyl Phenyl Ether | Phenol |
|---|---|---|
| 15 | 7 | 93 |

As shown in Table 13-2, in Test Example 15, after the reduction reaction, the concentration ratio of unreacted benzyl phenyl ether to phenol after the reduction was 7:93.

Test Example 16

In order to examine the presence or absence of the selectivity of the reduction reaction for an aromatic benzyl ether group by using the catalysts prepared in Examples 2 and 11, the catalytic activities were examined when 4-benzyloxyphenol was used as a reactant.

Test Example 16-1

4-Benzyloxyphenol was dissolved in 1 mL of methanol so as to be 0.25 mol/L The palladium-supported catalyst obtained in Example 2 was added so that the molar ratio of palladium of the catalyst to the reactant became 0, 1 mol %. The mixture was stirred at 25° C. for 24 hours under a hydrogen atmosphere. After the reaction, the concentration ratio of unreacted 4-benzyloxyphenol to 1,4-benzenediol after the reduction was analyzed by 1H-NMR Test Example 16-2

For the palladium-supported catalyst obtained in Example 11, the superiority and the inferiority of the catalytic activity were compared as in Test Example 16-1, except that the molar ratio of palladium of the catalyst to the reactant was 1 mol %, and the stirring time was three hours.

The results of comparing the catalytic activities are shown in the tables below. In Table 14-1, "used amount of catalyst [mol %]" means the molar ratio of palladium in the catalyst. Specifically, it means the molar ratio of palladium of the catalyst to the reactant.

TABLE 14-1

| Test Example | Pd Supported-Carrier | Pd Supporting Method | Supercritical Fluid or Organic Solvent | Type of Silica Gel | Supporting Amount of Pd [wt %] | Used Amount of Catalyst [mol %] | Reaction (Stirring) Time [hour] |
|---|---|---|---|---|---|---|---|
| 16-1 | Example 2 | Atmospheric Method | Acetonitrile | Bimodal Hierarchical Porous Structure | 3.5 | 0.1 | 24 |
| 16-2 | Example 11 | Supercritical Method | Carbon Dioxide | Bimodal Hierarchical Porous Structure | 4.4 | 1 | 3 |

TABLE 14-2

| Test Example | 4-benzyloxyphenol | 1,4-benzenediol |
|---|---|---|
| 16-1 | 97 | 3 |
| 16-2 | 0 | 100 |

As shown in Table 14-2, in Test Example 16-1, after the reduction reaction, the concentration ratio of unreacted 4-benzyloxyphenol to 1,4-benzenediol after the reduction was 97:3. In Test Example 16-2, after the reduction reaction, the concentration ratio of unreacted 4-benzyloxyphenol to 1,4-benzenediol after the reduction was 0:100. From the results of Test Example 16-1, it was confirmed that the catalytic activity was not exhibited for the aromatic benzyl ether group when the Pd-supported carrier of Example 2 was used, whereas the catalyst of the present invention supporting palladium by the supercritical method exhibited the catalytic activity.

Test Example 17

In order to examine the presence or absence of the selectivity of the reduction reaction for an aromatic epoxide group by using the catalyst prepared in Example 6, the catalytic activity was examined when styrene oxide was used as a reactant.

Styrene oxide was dissolved in 1 mL of methanol so as to be 0.25 mol/L. Then, the palladium-supported catalyst obtained in Example 6 was added so that the molar ratio of palladium of the catalyst to the reactant became 0.025 mol %. The mixture was stirred at 25° C. for two hours under a hydrogen atmosphere. After the reduction reaction, the concentration ratio among unreacted styrene oxide, and (2-hydroxyethyl)benzene, (1-hydroxyethyl)benzene, (2-hydroxy-1-methoxyethyl)benzene, and 2-phenylacetaldehyde after the reduction was analyzed by 1H-NMR.

The results of comparing the catalytic activities are shown in the tables below. In Table 15-1, "used amount of catalyst [mol %]" means the molar ratio of palladium in the catalyst. Specifically, it means the molar ratio of palladium of the catalyst to the reactant.

TABLE 15-1

| Test Example | Pd Supported-Carrier | Pd Supporting Method | Supercritical Fluid | Type of Silica Gel | Supporting Amount of Pd [wt %] | Used Amount of Catalyst [mol %] | Reaction (Stirring) Time [hour] |
|---|---|---|---|---|---|---|---|
| 17 | Example 6 | Supercritical Method | Carbon Dioxide | Bimodal Hierarchical Porous Structure | 0.25 | 0.025 | 2 |

TABLE 15-2

| Test Example | Styrene Oxide | (2-hydroxyethyl)benzene | (1-hydroxyethyl)benzene | (2-hydroxy-1-methoxyethyl)benzene | 2-phenyl-acetaldehyde |
|---|---|---|---|---|---|
| 17 | 0 | 99 | 0 | 0 | 1 |

As shown in Table 15-2, in Test Example 17, after the reduction reaction, the concentration ratio among unreacted styrene oxide, and (2-hydroxyethyl)benzene, (1-hydroxyethyl)benzene, (2-hydroxy-1-methoxyethyl)benzene and 2-phenylacetaldehyde after the reduction was 0:99:0:0:1. From the results of Test Example 17, it was confirmed that the catalyst of the present invention supporting palladium by the supercritical method exhibited catalytic activity for the aromatic epoxide group.

Test Example 18

In order to examine the presence or absence of the selectivity of the reduction reaction for an aliphatic benzyl ether group by using the catalysts prepared in Examples 6 and 11, the catalytic activities were examined when benzylnoninyl ether or benzyl decanyl ether was used as a reactant.

Test Example 18-1

Benzylnoninyl ether was dissolved in 1 mL of methanol so as to be 0.25 mol/L. Then, the palladium-supported catalyst obtained in Example 6 was added so that the molar ratio of palladium to the reactant became 0.025 mol % The mixture was stirred at 25° C. for six hours under a hydrogen atmosphere. After the reduction reaction, the concentration ratio of unreacted benzylnoninyl ether to nonanol after the reduction was analyzed by 1H-NMR Test Example 18-2

For the palladium-supported catalyst obtained in Example 11, the superiority and the inferiority of the catalytic activity were compared as in Test Example 18-1, except that the reactant was benzyldecanyl ether, the molar ratio of palladium of the catalyst to the reactant was 1 mol %, and the stirring time was 24 hours.

Test Example 18-3

For the palladium-supported catalyst obtained in Example 11, the superiority and the inferiority of the catalytic activity were compared as in Test Example 18-1, except that the reactant was benzyldecanyl ether, the molar ratio of palladium of the catalyst to the substrate was 1 mol %, and the stirring was at 40° C. for 24 hours under a hydrogen atmosphere.

The results of comparing the catalytic activities are shown in the tables below. In Table 16-1, "used amount of catalyst [mol %]" means the molar ratio of palladium in the catalyst. Specifically, it means the molar ratio of palladium of the catalyst to the reactant.

TABLE 16-1

| Test Example | Pd Supported-Carrier | Pd Supporting Method | Supercritical Fluid | Type of Silica Gel | Supporting Amount of Pd [wt %] | Used Amount of Catalyst [mol %] | Reaction (Stirring) Time [hour] | Reaction (Stirring) Temperature [° C.] |
|---|---|---|---|---|---|---|---|---|
| 18-1 | Example 6 | Supercritical Method | Carbon Dioxide | Bimodal Hierarchical Porous Structure | 0.25 | 0.025 | 6 | 25 |
| 18-2 | Example 11 | Supercritical Method | Carbon Dioxide | Bimodal Hierarchical Porous Structure | 4.4 | 1 | 24 | 25 |
| 18-3 | Example 11 | Supercritical Method | Carbon Dioxide | Bimodal Hierarchical Porous Structure | 4.4 | 1 | 24 | 40 |

TABLE 16-2

| Test Example | Benzylnoninyl Ether | 1-nonanol |
|---|---|---|
| 18-1 | 0 | 100 |

| Test Example | Benzyldecanyl Ether | 1-decanol |
|---|---|---|
| 18-2 | 59 | 41 |
| 18-3 | 0 | 100 |

As shown in Table 16-2, in Test Example 18-1, after the reduction reaction, the concentration ratio of unreacted benzylnoninyl ether to 1-nonanol after the reduction was 0:100. In Test Example 18-2, after the reduction reaction, the concentration ratio of unreacted benzyldecanyl ether to 1-decanol after the reduction was 59:41. In Test Example 18-3, after the reduction reaction, the concentration ratio of unreacted benzyldecanyl ether to 1-decanol after the reduction was 0:100. From the results of Test Examples 18-2 and 18-3, it was confirmed that the catalyst of the present invention supporting palladium by the supercritical method exhibited catalytic activity for the aliphatic benzyl ether group by stirring at 40° C. for 24 hours under a hydrogen atmosphere.

Test Example 19

In order to examine the presence or absence of the selectivity of the reduction reaction for aromatic aldehyde by using the catalyst prepared in Example 6, the catalytic activity was examined when p-anisaldehyde was used as a reactant.

p-anisaldehyde was dissolved in 1 mL of methanol so as to be 0.25 mol/L. Then, the palladium-supported catalyst obtained in Example 6 was added so that the molar ratio of palladium of the catalyst to the reactant became 0.025 mol %. The mixture was stirred at 25° C. for 18 hours under a hydrogen atmosphere. After the reduction reaction, the concentration ratio of unreacted p-anisaldehyde to anise alcohol after the reduction was analyzed by 1H-NMR.

The results of comparing the catalytic activities are shown in the tables below. In Table 17-1, "used amount of catalyst [mol %]" means the molar ratio of palladium in the catalyst. Specifically, it means the molar ratio of palladium of the catalyst to the reactant.

TABLE 17-1

| Test Example | Pd Supported Carrier | Pd Supporting Method | Supercritical Fluid | Type of Silica Gel | Supporting Amount of Pd [wt %] | Used Amount of Catalyst [mol %] | Reaction (Stirring) Time [hour] |
|---|---|---|---|---|---|---|---|
| 19 | Example 6 | Supercritical Method | Carbon Dioxide | Bimodal Hierarchical Porous Structure | 0.25 | 0.025 | 18 |

TABLE 17-2

| Test Example | p-anisaldehyde | Anise Alcohol |
|---|---|---|
| 19 | 12 | 88 |

As shown in Table 17-2, in Test Example 19, after the reduction reaction, the concentration ratio of unreacted p-anisaldehyde to anise alcohol after the reduction was 12:88. From the results of Test Example 19, it was confirmed that the catalyst of the present invention supporting palladium by the supercritical method exhibited catalytic activity for the aromatic benzyl ether group.

Test Example 20

In order to examine the presence or absence of the selectivity of the reduction reaction for an O-TES group by using the catalysts prepared in Examples 2, 6 and 11, the catalytic activities were examined when cinnamyloxytriethylsilane was used as a reactant.

Test Example 20-1

Cinnamloxytriethylsilane was dissolved in 1 mL of methanol so as to be 0.25 mol/L. Then, the palladium-supported catalyst obtained in Example 2 was added so that the molar ratio of palladium of the catalyst to the reactant became 0.1 mol %. The mixture was stirred at 25° C. for 23 hours under a hydrogen atmosphere. After the reduction reaction, the concentration ratio among unreacted cinnamloxytriethylsilane, and (3-phenylpropyloxy)triethoxysilane and 3-phenylpropanol after the reduction was analyzed by 1H-NMR Test Example 20-2

For the palladium-supported catalyst obtained in Example 6, the superiority and the inferiority of the catalytic activity were compared as in Test Example 20-1, except that the molar ratio of palladium of the catalyst to the reactant was 0.025 mol %, and the reaction time was 22 hours.

Test Example 20-3

For the palladium-supported catalyst obtained in Example 6, the superiority and the inferiority of the catalytic activity were compared as in Test Example 20-1, except that the molar ratio of palladium of the catalyst to the reactant was 0.025 mol %, ethyl acetate was used instead of methanol, and the reaction time was 22 hours.

Test Example 20-4

For the palladium-supported catalyst obtained in Example 11, the superiority and the inferiority of the catalytic activity were compared as in Test Example 20-1, except that the molar ratio of palladium of the catalyst to the reactant was 1 mol %, and the reaction time was 24 hours.

The results of comparing the catalytic activities are shown in the tables below. In Table 18-1, "used amount of catalyst [mol %]" means the molar ratio of palladium in the catalyst. Specifically, it means the molar ratio of palladium of the catalyst to the reactant.

TABLE 18-1

| Test Example | Pd Supported-Carrier | Pd Supporting Method | Supercritical Fluid or Organic Solvent | Type of Silica Gel | Supporting Amount of Pd [wt %] | Used Amount of Catalyst [mol %] | Reaction (Stirring) Time [hour] |
|---|---|---|---|---|---|---|---|
| 20-1 | Example 2 | Atmospheric Method | Acetonitrile | Bimodal Hierarchical Porous Structure | 3.5 | 0.1 | 23 |
| 20-2 | Example 6 | Supercritical Method | Carbon Dioxide | Bimodal Hierarchical Porous Structure | 0.25 | 0.025 | 22 |
| 20-3 | Example 6 | Supercritical Method | Carbon Dioxide | Bimodal Hierarchical Porous Structure | 0.25 | 0.025 | 22 |
| 20-4 | Example 11 | Supercritical Method | Carbon Dioxide | Bimodal Hierarchical Porous Structure | 4.4 | 1 | 24 |

TABLE 18-2

| Test Example | Cinnamyloxy-trimethylsilane | (3-phenylpropyloxy) Triethoxysilane | 3-phenylpropanol |
|---|---|---|---|
| 20-1 | 0 | 95 | 5 |
| 20-2 | 0 | 85 | 15 |
| 20-3 | 0 | 100 | 0 |
| 20-4 | 0 | 100 | 0 |

As shown in Table 18-2, in Test Example 20-1, after the reduction reaction, the concentration ratio among unreacted cinnamyloxytriethylsilane, and (3-phenylpropyloxy)triethoxysilane and 3-phenylpropanol after the reduction was 0:95:5. In Test Example 20-2, after the reduction reaction, the concentration ratio among unreacted cinnamyloxytriethylsilane, and (3-phenylpropyloxy)triethoxysilane and 3-phenylpropanol after the reduction was 0:85:15. In Test Examples 20-3 and 20-4, after the reduction reaction, the concentration among unreacted cinnamyloxytriethylsilane, and (3-phenylpropyloxy)triethoxysilane and 3-phenylpropanol after the reduction were 0:100:0. From these results, it was confirmed that all the catalysts of the present invention supporting palladium by the supercritical method and the atmospheric method hardly exhibited reduction catalytic activities for the O-TES group.

carbonyl group (ketone, aldehyde group) adjacent to an aromatic ring or a heteroaromatic ring, or the like, but selectively reduces only a nitro group, an alkenyl group, an azido group and an alkyne group, or can selectively reduce only an N-Cbz group if reaction conditions such as tem-

TABLE 19

|  | Alkyne (1, 2) | Azide (6, 7) | Alkene (1, 2, 5) | Nitro (3, 4) | Aromatic N-Cbz (8) | Alipathic N-Cbz (9) | Aromatic Keytone (10) |
|---|---|---|---|---|---|---|---|
| Pd/C | A | A | A | A | A | A | A |
| Pd/HP20 | A | A | A | A | A | A | A |
| Supercritically Pd-Supported Catalyst Obtained in Example 6 | A | A | A | A | A | A | A |
| Pd/C + NH$_4$OAc | A | A | A | A | A | A | A |
| Pd/WA30 | A | A | A | A | A | A | A |
| Pd/CR11 | A | A | A | A | A | A | A |
| Pd/CR20 | A | A | A | A | A | A | A |
| Pd/C/(en) | A | A | A | A | A | C | A |
| Pd/ceramic | A | A | A | A | A | A | B |
| Atmospherically Pd-Supported Catalyst Obtained in Example 2 | A | A | A | A | B | C | C |
| Pd/C(Ph$_2$S) | A | A | A | B** | C | C | C |
| Pd/Fib | A | A | A | B | C | C | C |
| Pd/MS3A | A | A | A | C | C | C | C |
| Pd/BN | A | A | A | C | C | C | C |
| Pd/PEI | A | B | C | C | C | C | C |
| Pd/BN + Pyridine | A | C | C | C | C | C | C |

|  | Benzyl Ester (12, 13) | Aromatic Chlorine (14) | Aromatic Benzyl Ether (15, 16) | Aromatic Epoxide (17) | Aromatic Benzyl Ether (18) | Aromatic Aldehyde (19) | O-TES Group (20) |
|---|---|---|---|---|---|---|---|
| Pd/C | A | A | A | A | A | A | A |
| Pd/HP20 | A | A | A | A | A | A | A |
| Supercritically Pd-Supported Catalyst Obtained in Example 6 | B | A | A | A | A | A | C |
| Pd/C + NH$_4$OAc | A | A | A | A | C | C | C |
| Pd/WA30 | A | A | A | A**** | C | C | C |
| Pd/CR11 | A | A | A | C | C | C | C |
| Pd/CR20 | A | A | A | C | C | C | C |
| Pd/C/(en) | A | A | C | A**** | C | C | C |
| Pd/ceramic | C | C | C | C | C | C | C |
| Atmospherically Pd-Supported Catalyst Obtained in Example 2 | C | C* | C | C* | C* | C | C |
| Pd/C(Ph$_2$S) | C | C | C | C | C | C | C |
| Pd/Fib | C | C | C | C | C | C | C |
| Pd/MS3A | C | C | C | C | C | C | C |
| Pd/BN | C | C | C | C | C | C | C |
| Pd/PEI | C | C | C | C | C | C | C |
| Pd/BN + Pyridine | C | C | C | C | C | C | C |

A: Catalytic activity present
B: Catalytic activity present under some conditions
C: No catalytic activity
*Not examined
**Not examined Org. Lett., 2006, 8, 3279, Tetrahedron, 2006, 62, 11925.
***Adv. Synth. Catal. 2017, 359, 2269.
****Chem. commun., 1999, 1047, Chem. Eur. J., 2000, 6, 2204.

When the catalytic activities for the respective substrates used in Test Examples are arranged in the order of catalytic activity present (A), catalytic activity present under some conditions (B) and no catalytic activity (C), there is a tendency for the selectivity of the reduction reaction as shown in Table 19. Note that the number in the parentheses written next to the reactant means the number of Test Example. The atmospherically Pd-supported catalyst obtained in Example 2 exhibits the strength of the catalytic activity between Pd/cearamic and Pd/C (Ph$_2$S), indicating specific selectivity for the reduction reaction. Specifically, the atmospherically Pd-supported catalyst obtained in Example 2 is a catalyst that does not reduce an epoxide group, a benzyl ether groups, a halogen atom on an aromatic ring or a heteroaromatic ring, a benzyl ester group, a perature and time are selected. The reactivity for aromatic chlorine, aromatic epoxide and aliphatic benzyl ether has not been examined. However, from the tendency for the reactivity of other palladium catalysts, the atmospherically Pd-supported catalyst obtained in Example 2 is considered not to have catalytic activity for aromatic chlorine, aromatic epoxide and aliphatic benzyl ether.

The supercritically Pd-supported catalyst obtained in Example 6 exhibits the strength of the catalytic activity between Pd/C, Pd/HP20 and Pd/C+NH$_4$OAc, indicating specific selectivity for the reduction reaction. Specifically, the supercritically Pd-supported catalyst obtained in Example 6 differs from Pd/C. Pd/HP20 and Pd/C+NH$_4$OAc in that the catalyst can non-selectively or selectively reduce only a specific functional group such as an epoxide group, a benzyl ether group, a halogen atom on an aromatic ring or a heteroaromatic ring, a benzyl ester group, a carbonyl group (ketone, aldehyde group) adjacent to an aromatic ring or a heteroaromatic ring, a nitrogen-bonded benzyloxycarbonyl group (N-Cbz group), a nitro group, an alkenyl group, an azido group or an alkyne group in a molecule when an oxygen-bonded trialkylsilyl group (such as an O-TES group) is present in the molecule together with the functional group such as an epoxide group, a benzyl ether group, a halogen atom on an aromatic ring or a heteroaromatic ring, a benzyl ester group, a carbonyl group (ketone, aldehyde group) adjacent to an aromatic ring or a heteroaromatic ring, a nitrogen-bonded benzyloxycarbonyl group (N-Cbz group), a nitro group, an alkenyl group, an azido group or an alkyne group, but cannot reduce the silyl group.

In Table 19, Pd/C means an activated carbon-supported catalyst, Pd/HP20 means a polystyrene-based synthetic adsorbent diaion-supported catalyst manufactured by Mitsubishi Chemical Corporation. Pd/C+NH$_4$OAc means an ammonium acetate-added activated carbon-supported catalyst, Pd/WA30 means a styrene-based dimethylamine type diaion-supported catalyst manufactured by Mitsubishi Chemical Corporation, Pd/CR11 means an iminodiacetic acid type diaion-supported catalyst manufactured by Mitsubishi Chemical Corporation. Pd/CR20 means a polyamine type diaion-supported catalyst manufactured by Mitsubishi Chemical Corporation, Pd/ceramic means a ceramic-supported catalyst. Pd/C(en) means an ethylenediamine-added activated carbon-supported catalyst, Pd/C(Ph$_2$S) means a biphenylthioether-supported catalyst, Pd/Fib means a fibroin (silk)-supported catalyst manufactured by FUJIFILM Wako Pure Chemical Corporation. Pd/MS3A means a molecular sieves 3A-supported catalyst, Pd/BN means a boron nitride-supported catalyst, Pd/PEI means polyethyleneimine-supported catalyst, and Pd/BN+Pyridine means pyridine-added boron nitride-supported catalyst Oxidation Reaction The metal-supported catalyst of the present invention can also be used as a heterogeneous catalyst for oxidation reaction. Examples of the oxidation reaction include a dehydrogenative oxidation reaction of alcohol.

Test Example 21

As an example of the dehydrogenative oxidation reaction of alcohol, the catalytic activity was examined using the catalyst prepared in Example 6 when p-methylbenzyl alcohol was used as a reactant.

p-methylbenzyl alcohol as a reactant was dissolved in 1 mL of methanol to be 0.25 mol/L. Then, the palladium-supported catalyst obtained in Example 6 was added so that the molar ratio of palladium of the catalyst to the reactant became 0.025 mol %. The mixture was stirred at 25° C. for 24 hours under a hydrogen atmosphere. After stirring for 24 hours, the concentration ratio of unreacted p-methylbenzyl alcohol to p-methylbenzaldehyde after the reaction was analyzed by 1H-NMR, and the concentration ratio of unreacted p-methylbenzyl alcohol to p-methylbenzaldehyde after the reaction was 79:21.

From the above results, it was confirmed that the catalyst of the present invention supporting palladium by the supercritical method exhibited slight catalytic activity in the dehydrogenative oxidation reaction of benzyl alcohol. Moreover since the reaction was conducted under a hydrogen atmosphere, it is assumed that the reduction reaction of the aromatic aldehyde is also in equilibrium as described in the reduction reaction of aromatic aldehyde in Test Example 19. That is, it is considered that p-methylbenzaldehyde after the reaction is reduced again to generate p-methylbenzyl alcohol, and the dehydrative oxidation reaction and the reduction reaction are in equilibrium. In other words, in Test Example 19, it is considered that the anise alcohol after the reaction is partially in equilibrium with the dehydrative oxidation reaction, and p-anisaldehyde is generated.

The invention claimed is:

1. A catalyst comprising:
    a granular carrier; and
    a metal obtained by reducing a metal ion supported on the granular carrier 1) in a supercritical state or 2) in a polar organic solvent,
    the granular carrier having a skeleton body composed of an inorganic compound comprising silica or titania, with a three-dimensional continuous network structure,
    the skeleton body having a bimodal hierarchical porous structure composed of a through-hole and a pore, the through-hole being formed in a void of the skeleton body, and the pore being extending from a surface to an inside of the skeleton body and dispersively formed on the surface,
    wherein a most frequent diameter of the pore, measured in nm, is within a range of 2 nm or more and 80 nm or less;
    wherein a most frequent diameter of the through-hole, measured in μm, is equal to or greater than five times the most frequent pore diameter of the pore, measured in nm, and is within a range of 0.1 μm or more and 10 μm or less, and
    wherein the metal is a platinum group element and/or a group 10 element.

2. The catalyst according to claim 1, wherein a supporting amount of the metal is 0.01 to 30 wt % based on 100 wt % of the catalyst.

3. The catalyst according to claim 1, wherein a supporting amount of the metal supported 2) in the polar organic solvent is 0.01 to 30 wt % based on 100 wt % of the catalyst.

4. The catalyst according to claim 1, wherein the polar organic solvent is at least one selected from the group consisting of methanol, acetonitrile, acetone, 2-propanol and tetrahydrofuran.

5. The catalyst according to claim 1, wherein a supporting amount of the metal supported 1) in the supercritical state is 0.01 to 6 wt % based on 100 wt % of the catalyst.

6. A method for producing the catalyst according to claim 1, the method comprising:
    a step of causing the granular carrier to support the metal ion 1) in the supercritical state or 2) in the polar organic solvent; and
    a step of reducing the metal ion to the metal.

7. The method for producing the catalyst according to claim 6, wherein a supporting amount of the metal is 0.01 to 30 wt % based on 100 wt % of the catalyst.

8. The method for producing the catalyst according to claim 6, wherein a supporting amount of the metal supported 2) in the polar organic solvent is 0.01 to 30 wt % based on 100 wt % of the catalyst.

9. The method for producing the catalyst according to claim 6, wherein the polar organic solvent is at least one selected from the group consisting of methanol, acetonitrile, acetone, 2-propanol and tetrahydrofuran.

10. The method for producing the catalyst according to claim 6, wherein a supporting amount of the metal supported 1) in the supercritical state is 0.01 to 6 wt % based on 100 wt % of the catalyst.

11. A method for producing the catalyst according to claim 1, the method comprising:
- a step of causing the inorganic porous body having the hierarchical porous structure to support the metal ion 1) in the supercritical state or 2) in the polar organic solvent; and
- a step of reducing the metal ion to the metal.

12. A reduction method comprising a step of reducing a reactant by using the catalyst according to claim 1.

13. A reduction method comprising a step of reducing a reactant (excluding styrene as the reactant) by using the catalyst according to claim 1.

14. The reduction method according to claim 12, wherein the reactant is a compound having an alkynyl group, an alkenyl group, an azido group, a nitro group, an N-Cbz group, a ketone group or an aldehyde group adjacent to an aromatic ring or a heteroaromatic ring, a benzyl ester group, a halogen atom on an aromatic ring or a heteroaromatic ring, a benzyl ether group, an epoxide group, or an N-Cbz group, and optionally having in a molecule a substituent of an alkyl group, an aromatic ring or a heteroaromatic ring resistant to reduction.

15. The catalyst according to claim 1, wherein a particle diameter of the granular carrier, measured in μm, is equal to or greater than five times the most frequent diameter of the through-hole, measured in μm, and is within a range of 20 μm or more and 250 μm or less.

16. The catalyst according to claim 1, wherein the metal is palladium.

* * * * *